(12) United States Patent
Bettati et al.

(10) Patent No.: US 7,005,431 B2
(45) Date of Patent: Feb. 28, 2006

(54) IMIDAZO-TRIAZINE DERIVATIVES AS LIGANDS FOR GABA RECEPTORS

(75) Inventors: Michela Bettati, Sawbridgeworth (GB); Mark Stuart Chambers, Puckeridge (GB); Simon Charles Goodacre, Benington (GB); David James Hallett, Watford (GB); Michael Geoffrey Neil Russell, Welwyn Garden City (GB); Leslie Jospeh Street, Little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/512,655

(22) PCT Filed: May 1, 2003

(86) PCT No.: PCT/GB03/01888

§ 371 (c)(1),
(2), (4) Date: Oct. 29, 2004

(87) PCT Pub. No.: WO03/093272

PCT Pub. Date: Nov. 13, 2003

(65) Prior Publication Data

US 2005/0165023 A1  Jul. 28, 2005

(30) Foreign Application Priority Data

May 2, 2002  (GB)  .................................. 0210124

(51) Int. Cl.
*C07D 487/04*  (2006.01)
*A61K 31/4188*  (2006.01)
*A61P 25/22*  (2006.01)
*A61P 25/28*  (2006.01)

(52) U.S. Cl. ...................................... 514/243; 544/184
(58) Field of Classification Search ................ 544/184; 514/243

See application file for complete search history.

(56) References Cited

U.S. PATENT DOCUMENTS 6,617,326 B1 * 9/2003 Carling et al. ............... 514/243
6,696,444 B1 * 2/2004 Carling et al. ............... 514/243

FOREIGN PATENT DOCUMENTS

WO   WO 00 23449 A   4/2000
WO   WO 01 77111 A   10/2001

OTHER PUBLICATIONS

Scott et al. Prog. Med. Chem. 36: 169-200,1999.*

* cited by examiner

*Primary Examiner*—Venkataraman Balasubramanian
(74) *Attorney, Agent, or Firm*—J. Eric Thies; Melvin Winokur

(57) ABSTRACT

A class of 7-phenylimidazo[1,2-b][1,2,4]triazine derivatives, substituted at the meta position of the phenyl ring by an optionally substituted aryl or heteroaryl group which is directly attached or bridged by an oxygen atom or a —NH— linkage, and substituted on the phenyl ring by one or two further substituents as defined herein, being selective ligands for $GABA_A$ receptors, in particular having good affinity for the α2 and/or α3 and/or α5 subunit thereof, are accordingly of benefit in the treatment and/or prevention of adverse conditions of the central nervous system, including anxiety, convulsions and cognitive disorders.

10 Claims, No Drawings

US 7,005,431 B2

IMIDAZO-TRIAZINE DERIVATIVES AS LIGANDS FOR GABA RECEPTORS

CROSS REFERENCE TO RELATED APPLICATIONS

This application is a U.S. National Phase application under 35 U.S.C. §371 of PCT Application No. PCT/GB03/01888, filed May 1, 2003, which claims priority under 35 U.S.C. § 119 from GB Application No. 0210124.4, filed May 2, 2002.

The present invention relates to a class of substituted imidazo-triazine derivatives and to their use in therapy. More particularly, this invention is concerned with imidazo [1,2-b][1,2,4]triazine analogues which are substituted in the 7-position by a substituted phenyl ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta\gamma1$, $\alpha2\beta2/3\gamma2$, $\alpha3\beta\gamma2/3$, $\alpha4\beta\delta$, $\alpha5\beta3\gamma2/3$, $\alpha6\beta\gamma2$ and $\alpha6\beta\delta$. Subtype assemblies containing an $\alpha1$ subunit are present in most areas of the brain and are thought to account for over 40% of $GABA_A$ receptors in the rat. Subtype assemblies containing $\alpha2$ and $\alpha3$ subunits respectively are thought to account for about 25% and 17% of $GABA_A$ receptors in the rat. Subtype assemblies containing an $\alpha5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect.

Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha1$ subunit in combination with a $\beta$ subunit and $\gamma2$. This is the most abundant $GABA_A$ receptor subtype, and is believed to represent almost half of all $GABA_A$ receptors in the brain.

Two other major populations are the $\alpha2\beta\gamma2$ and $\alpha3\beta\gamma2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta\gamma2$, $\alpha2\beta\gamma2$ or $\alpha3\beta\gamma2$ subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha1$ subunit. Accordingly, it is considered that $GABA_A$ receptor agonists which interact more favourably with the $\alpha2$ and/or $\alpha3$ subunit than with $\alpha1$ will be effective in the treatment of anxiety with a reduced propensity to cause sedation. Moreover, agents which are inverse agonists of the $\alpha5$ subunit are likely to be beneficial in enhancing cognition, for example in subjects suffering from dementing conditions such as Alzheimer's disease. Also, agents which are antagonists or inverse agonists at $\alpha1$ might be employed to reverse sedation or hypnosis caused by $\alpha1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; Tourette's syndrome; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for GABA$_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human GABA$_A$ receptor.

The present invention provides a class of imidazo-triazine derivatives which possess desirable binding properties at various GABA$_A$ receptor subtypes. The compounds in accordance with the present invention have good affinity as ligands for the α2 and/or α3 and/or α5 subunit of the human GABA$_A$ receptor. The compounds of this invention may interact more favourably with the α2 and/or α3 subunit than with the α1 subunit; and/or may interact more favourably with the α5 subunit than with the α1 subunit.

The compounds of the present invention are GABA$_A$ receptor subtype ligands having a binding affinity ($K_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or a salt or prodrug thereof:

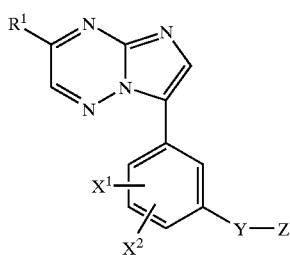

(I)

wherein

X$^1$ represents C$_{1-6}$ alkyl, trifluoromethyl, hydroxy or C$_{1-6}$ alkoxy, and X$^2$ represents hydrogen; or X$^1$ represents halogen, C$_{1-6}$ alkyl, trifluoromethyl, hydroxy or C$_{1-6}$ alkoxy, and X$^2$ represents halogen;

Y represents a chemical bond, an oxygen atom, or a —NH— linkage;

Z represents an optionally substituted aryl or heteroaryl group;

R$^1$ represents hydrogen, hydrocarbon, a heterocyclic group, halogen, cyano, trifluoromethyl, nitro, —OR$^a$, —SR$^a$, —SOR$^a$, —SO$_2$R$^a$, SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and R$^a$ and R$^b$ independently represent hydrogen, hydrocarbon or a heterocyclic group.

The aryl or heteroaryl group Z in the compounds of formula I above may be unsubstituted, or substituted by one or more substituents. Typically, the group Z will be unsubstituted, or substituted by one or two substituents. Typical substituents on the group Z include halogen, cyano, nitro, C$_{1-6}$ alkyl, hydroxy, C$_{1-6}$ alkoxy, oxy, C$_{1-6}$ alkylsulphonyl, amino, aminocarbonyl, formyl, C$_{2-6}$ alkoxycarbonyl and —CR$^a$=NOR$^b$, wherein R$^a$ and R$^b$ are as defined above.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands. e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, indanyl, aryl and aryl(C$_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "C$_{1-6}$ alkoxy", "C$_{1-6}$ alkylamino" and "C$_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of C$_{3-7}$ cycloalkyl(C$_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, alylcarbonyl, $C_{1-6}$ alkylthio, $C_{1-6}$ alkylsulphinyl, $C_{1-6}$ alkylsulphonyl, arylsulphonyl, —$NR^vR^w$, —$NR^vCOR^w$, —$NR^vCO_2R^w$, —$NR^vSO_2R^w$, —$CH_2NR^vSO_2R^w$, —$CH_2NR^vSO_2R^w$, —$NHCONR^vR^w$, —$CONR^vR^w$, —$SO_2NR^vR^w$, and —$CH_2SO_2NR^vR^w$, in which $R^v$ and $R^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

The present invention includes within its scope prodrugs of the compounds of formula I above. In general such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Where $X^2$ represents hydrogen, suitable values of $X^1$ include methyl, trifluoromethyl, hydroxy and methoxy. In one embodiment, $X^1$ represents methyl and $X^2$ represents hydrogen.

Where $X^2$ represents halogen, suitable values of $X^1$ include fluoro, chloro, methyl, trifluoromethyl, hydroxy and methoxy. Preferably, $X^2$ is fluoro. In one embodiment, $X^1$ and $X^2$ are both fluoro. In another embodiment, $X^1$ is hydroxy and $X^2$ is fluoro.

In a preferred embodiment, Y represents a chemical bond.
In another embodiment, Y represents an oxygen atom.
In a further embodiment, Y represents a —NH— linkage.

Selected values for the substituent Z include phenyl, pyridinyl, pyridazinyl, pyrimidinyl, pyrazinyl, furyl, thienyl, oxazolyl, isoxazolyl, thiazolyl, isothiazolyl, pyrrolyl, pyrazolyl, imidazolyl, oxadiazolyl, thiadiazolyl, triazolyl and tetrazolyl, any of which groups may be optionally substituted by one or more substituents.

In one favoured embodiment, Z represents an optionally substituted phenyl group, in particular monosubstituted or disubstituted phenyl. In another favoured embodiment, Z represents optionally substituted pyridinyl, especially unsubstituted, monosubstituted or disubstituted pyridin-2-yl, pyridin-3-yl or pyridin-4-yl.

Examples of suitable substituents on the group Z include fluoro, chloro, cyano, nitro, methyl, hydroxy, methoxy, oxy, methanesulphonyl, amino, aminocarbonyl, formyl, methoxycarbonyl and —CH=NOH.

Examples of particular substituents on the group Z include fluoro and cyano.

Detailed values of Z include cyanophenyl, (cyano)(fluoro)phenyl, (chloro)(cyano)phenyl, nitrophenyl, methoxyphenyl, methanesulphonylphenyl, pyridinyl, fluoro-pyridinyl, difluoro-pyridinyl, (amino)(chloro)pyridinyl, cyano-pyridinyl, methyl-pyridinyl, hydroxypyridinyl, methoxypyridinyl, oxy-pyridinyl, aminocarbonyl-pyridinyl, pridazinyl, pyrimidinyl, pyrazinyl, cyano-thienyl, aminocarbonyl-thienyl, formyl-thienyl, methoxycarbonyl-thienyl, thienyl-CH=NOH, thiazolyl, isothiazolyl, pyrrolyl, pyrazolyl, imidazolyl, triazolyl and methyl-tetrazolyl.

Specific values of Z include (cyano)(fluoro)phenyl and pyridinyl.

In one embodiment, Z represents 2-cyano-4-fluorophenyl.
In another embodiment, Z represents 2-cyano-6-fluorophenyl.
In a further embodiment, Z represents pyridin-3-yl.
In an additional embodiment, Z represents pyridin-4-yl.

Typically, $R^1$ represents hydrogen, hydrocarbon, a heterocyclic group, halogen, cyano, trifluoromethyl, —$COR^a$, —$CO_2R^a$ or —$CR^a$=$NOR^b$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl, especially hydrogen or dimethylaminoethyl.

Suitable values of $R^1$ include hydrogen, $C_{1-6}$ alkyl, halo($C_{1-6}$)alkyl, dihalo($C_{1-6}$)alkyl, hydroxy($C_{1-6}$)alkyl, dihydroxy($C_{1-6}$)alkyl, $C_{1-6}$ alkoxy($C_{1-6}$)alkyl, di($C_{1-6}$)alkoxy($C_{1-6}$)alkyl, cyano($C_{1-6}$)alkyl, $C_{2-6}$ alkoxycarbonyl($C_{1-6}$) alkyl, heteroaryl, $C_{1-6}$ alkyl-heteroaryl, heteroaryl($C_{1-6}$) alkyl, halogen, cyano, trifluoromethyl, formyl, $C_{2-6}$ alkylcarbonyl, $C_{2-6}$ alkoxycarbonyl and —$CR^a$=$NOR^b$, in which $R^a$ and $R^b$ are as defined above.

Suitably, $R^1$ represents hydroxy,($C_{1-6}$)alkyl, halo($C_{1-6}$) alkyl or trifluoromethyl.

Individual values of $R^1$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), pyridinyl, furyl, thienyl, oxazolyl, methylthiazolyl, methyloxadiazolyl, imidazolylmethyl, triazolylmethyl, chloro, cyano, trifluoromethyl, formyl, acetyl, methoxycarbonyl and —CR$^2$=NOR$^3$, in which R$^2$ represents hydrogen or methyl, and R$^3$ represents hydrogen, hydroxyethyl or dimethylaminoethyl.

In one embodiment, R$^1$ represents 2-hydroxyprop-2-yl. In another embodiment, R$^1$ represents 2-fluoroprop-2-yl. In a further embodiment, R$^1$ represents trifluoromethyl.

Suitably, R$^2$ is hydrogen.

Suitably, R$^3$ represents hydrogen or dimethylaminoethyl, especially hydrogen.

A particular sub-class of compounds according to the invention is represented by the compounds of formula IIA, and salts and prodrugs thereof:

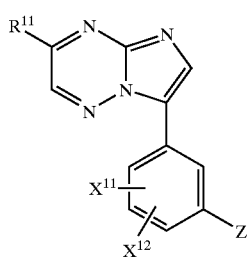

(IIA)

wherein

Z is as defined above;

X$^{11}$ represents methyl, trifluoromethyl, hydroxy or methoxy, and X$^{12}$ represents hydrogen; or X$^{11}$ represents fluoro, chloro, methyl, trifluoromethyl, hydroxy or methoxy, and X$^{12}$ represents fluoro;

R$^{11}$ represents hydrogen, C$_{1-6}$ alkyl, halo (C$_{1-6}$)alkyl, dihalo(C$_{1-6}$)alkyl, hydroxy(C$_{1-6}$)alkyl, dihydroxy(C$_{1-6}$)alkyl, C$_{1-6}$ alkoxy(C$_{1-6}$)alkyl, di(C$_{1-6}$)alkoxy(C$_{1-6}$)alkyl, cyano(C$_{1-6}$)alkyl, C$_{2-6}$ alkoxycarbonyl(C$_{1-6}$)alkyl, heteroaryl, C$_{1-6}$ alkyl-heteroaryl, heteroaryl(C$_{1-6}$)alkyl, halogen, cyano, trifluoromethyl, formyl, C$_{2-6}$ alkylcarbonyl, C$_{2-6}$ alkoxycarbonyl or —CR$^4$=NOR$^5$;

R$^4$ represents hydrogen or C$_{1-6}$ alkyl; and

R$^5$ represents hydrogen, C$_{1-6}$ alkyl, hydroxy(C$_{1-6}$)alkyl or di(C$_{1-6}$)alkylamino(C$_{1-6}$)alkyl.

Suitably, X$^{11}$ is methyl and X$^{12}$ is hydrogen.

Suitably, X$^{11}$ and X$^{12}$ are both fluoro.

Suitably, X$^{11}$ is hydroxy and X$^{12}$ is fluoro.

Suitably, R$^4$ represents hydrogen or methyl, especially hydrogen.

Suitably, R$^5$ represents hydrogen, methyl, ethyl, hydroxyethyl or dimethylaminoethyl. Particular values of R$^5$ include hydrogen, hydroxyethyl and dimethylaminoethyl. Typically, R$^5$ represents hydrogen or dimethylaminoethyl, especially hydrogen.

Where R$^{11}$ represents heteroaryl, this group is suitably pyridinyl, furyl, thienyl or oxazolyl.

Where R$^{11}$ represents C$_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where R$^{11}$ represents heteroaryl(C$_{1-6}$)alkyl, this group is suitably imidazolylmethyl or triazolylmethyl.

Suitably, R$^{11}$ represents hydroxy(C$_{1-6}$)alkyl, fluoro(C$_{1-6}$) alkyl or trifluoromethyl.

Individual values of R$^{11}$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), dihydroxypropyl (especially 1,2-dihydroxyprop-2-yl), fluoropropyl (especially 2-fluoroprop-2-yl), cyanopropyl (especially 2-cyanoprop-2-yl), methoxycarbonylpropyl (especially 2-methoxycarbonylprop-2-yl), tert-butyl, hydroxybutyl (especially 1-hydroxy-2-methylprop-2-yl), pyridinyl, furyl, thienyl, oxazolyl, methylthiazolyl, methyloxadiazolyl, imidazolylmethyl, triazolylmethyl, chloro, cyano, trifluoromethyl, formyl, acetyl, methoxycarbonyl and —CR$^2$=NOR$^3$, in which R$^2$ and R$^3$ are as defined above.

In one embodiment, R$^{11}$ represents 2-hydroxyprop-2-yl. In another embodiment, R$^{11}$ represents 2-fluoroprop-2-yl. In a further embodiment, R$^{11}$ represents trifluoromethyl.

One representative subset of the compounds of formula IIA above is represented by the compounds of formula IIB, and salts and prodrugs thereof:

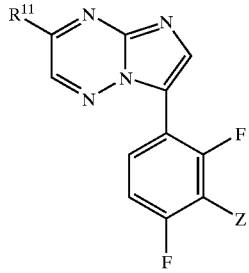

(IIB)

wherein Z and R$^{11}$ are as defined above.

Another representative subset of the compounds of formula IIA above is represented by the compounds of formula IIC, and salts and prodrugs thereof:

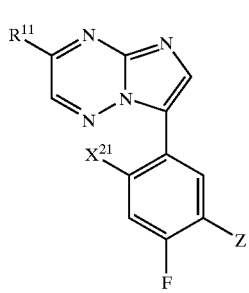

(IIC)

wherein Z and R$^{11}$ are as defined above; and

X$^{21}$ represents fluoro, chloro, methyl, trifluoromethyl, hydroxy or methoxy.

Particular values of X$^{21}$ include hydroxy and methoxy, especially hydroxy.

An additional representative subset of the compounds of formula IIA above is represented by the compounds of formula IID, and salts and prodrugs thereof:

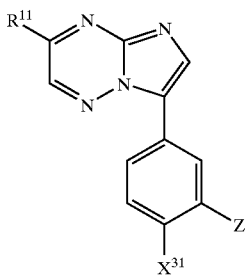

(IID)

wherein Z and R[11] are as defined above; and

X[31] represents methyl, trifluoromethyl, hydroxy or methoxy.

A particular value of X[31] is methyl.

Specific compounds within the scope of the present invention include:

2-{7-[2,4-difluoro-3-(pyridin-4-yl)phenyl]imidazo[1,2-b][1,2,4]triazin-3-yl}propan-2-ol;

3'-[3-(1-hydroxy-1-methylethyl)imidazo[1,2-b][1,2,4]triazin-7-yl]-6,2',6'-trifluorobiphenyl-2-carbonitrile;

3'-[3-(1-fluoro-1-methylethyl)imidazo[1,2-b][1,2,4]triazin-7-yl]-4,2',6'-trifluorobiphenyl-2-carbonitrile;

7-[2,4-difluoro-3-(pyridin-3-yl)phenyl]-3-trifluoromethylimidazo[1,2-b][1,2,4]triazine;

7-[4-methyl-3-(pyridin-3-yl)phenyl]-3-trifluoromethylimidazo[1,2-b][1,2,4]triazine;

6,2'-difluoro-4'-hydroxy-5'-[3-(1-hydroxy-1-methylethyl)imidazo[1,2-b][1,2,4]triazin-7-yl]biphenyl-2-carbonitrile;

3'-[3-(1-hydroxy-1-methylethyl)imidazo[1,2-b][1,2,4]triazin-7-yl]-4,2',6'-trifluorobiphenyl-2-carbonitrile;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the $\alpha 3$ subunit of the human $GABA_A$ receptor is conveniently as measured in the assay described hereinbelow. The $\alpha 3$ subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the $\alpha 3$ subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the $\alpha 1$ subunit of the human $GABA_A$ receptor.

The potentiation of the GABA $EC_{20}$ response in stably transfected cell lines expressing the $\alpha 3$ and $\alpha 1$ subunits of the human $GABA_A$ receptor can conveniently be measured by procedures analogous to the protocol described in Wafford et al., Mol. Pharmacol., 1996, 50, 670–673. The procedure will suitably be carried out utilising cultures of stably transfected eukaryotic cells, typically of stably transfected mouse Ltk⁻ fibroblast cells.

The compounds according to the present invention may exhibit anxiolytic activity, as may be demonstrated by a positive response in the elevated plus maze and conditioned suppression of drinking tests (cf. Dawson et al., Psychopharmacology, 1995, 121, 109–117). Moreover, the compounds of the invention are likely to be substantially non-sedating, as may be confirmed by an appropriate result obtained from the response sensitivity (chain-pulling) test (cf. Bayley et al., J. Psychopharmacol., 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in J. Pharmacol. Exp. Ther., 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, Psychobiology, 1993, 21, 101–108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds win be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixers and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

(III)

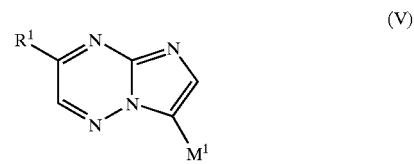

(IV)

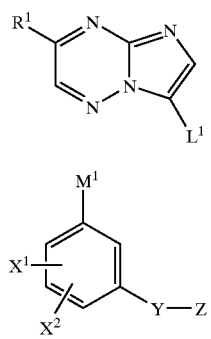

wherein $X^1$, $X^2$, Y, Z and $R^1$ are as defined above, $L^1$ represents a suitable leaving group, and $M^1$ represents a boronic acid moiety —$B(OH)_2$ or a cyclic ester thereof formed with an organic diol, e.g. pinacol, 1,3-propanediol or neopentyl glycol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. bromo.

The transition metal catalyst of use in the reaction between compounds III and IV is suitably tetrakis(triphenylphosphine)palladium(O). The reaction is conveniently carried out at an elevated temperature in a solvent such as 1,2-dimethoxyethane, N,N-dimethylacetamide, 1,4-dioxane or tetrahydrofuran, advantageously in the presence of potassium phosphate, copper(I) iodide, sodium carbonate or cesium carbonate. Alternatively, the transition metal catalyst employed may be dichloro [1,1'-bis(diphenylphosphino)ferrocene]palladium(II), in which case the reaction is conveniently effected at an elevated temperature in a solvent such as N,N-dimethylformamide, advantageously in the presence of potassium phosphate.

In an alternative procedure, the compounds according to the present invention may be prepared by a process which comprises reacting a compound of formula V with a compound of formula VI:

(V)

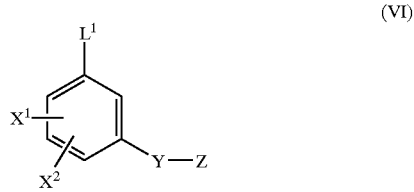

(VI)

wherein $X^1$, $X^2$, Y, Z, $R^1$, $L^1$ and $M^1$ are as defined above; in the presence of a transition metal catalyst; under conditions analogous to those described above for the reaction between compounds III and IV.

In another procedure, the compounds according to the present invention in which Y represents a chemical bond may be prepared by a process witch comprises reacting a compound of formula VII with a compound of formula VIII:

(VII)

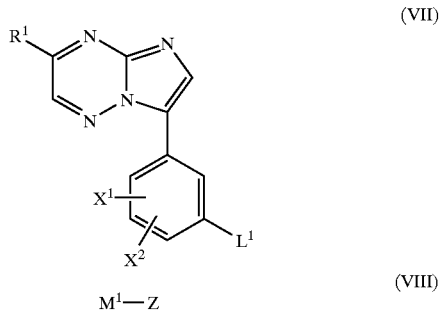

(VIII)

wherein $X^1$, $X^2$, Z, $R^1$, $L^1$ and $M^1$ are as defined above; in the presence of a transition metal catalyst; under conditions analogous to those described above for the reaction between compounds III and IV.

In the compounds of formula VI and VII above, the leaving group $L^1$ is typically trifluoromethanesulfonyloxy (triflyloxy); or a halogen atom, e.g. bromo.

Alternatively, the compounds according to the present invention in which Y represents a chemical bond may be prepared by a process which comprises reacting a compound of formula IX with a compound of formula X:

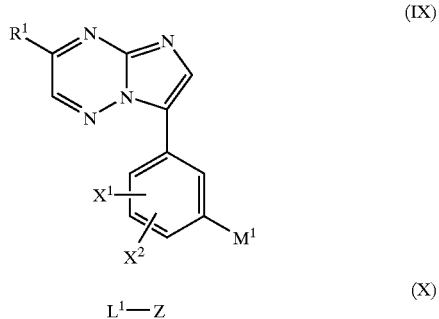

(IX)

L¹—Z (X)

wherein $X^1$, $X^2$, Z, $R^1$, $L^1$ and $M^1$ are as defined above; in the presence of a transition metal catalyst; under conditions analogous to those described above for the reaction between compounds III and IV.

In an additional procedure, the compounds according to the present invention in which Y represents an oxygen atom may be prepared by a process which comprises reacting a compound of formula X as defined above with a compound of formula XI:

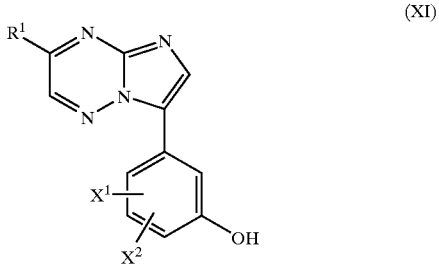

(XI)

wherein $X^1$, $X^2$ and $R^1$ are as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention in which Y represents a —NH— linkage may be prepared by a process which comprises reacting a compound of formula X as defined above with a compound of formula XII:

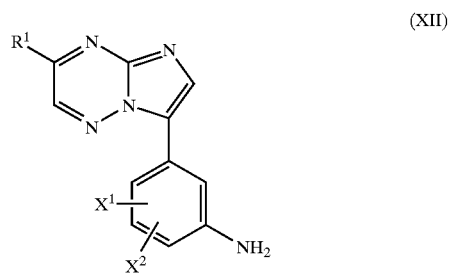

(XII)

wherein $X^1$, $X^2$ and $R^1$ are as defined above.

In relation to the reaction between compounds X and XII, the leaving group $L^1$ in the compounds of formula X may suitably represent fluoro.

The reaction between compounds X and XII is conveniently carried out by heating the reactants, typically at a temperature in the region of 120° C., in a solvent such as N,N-dimethylformamide.

Where $M^1$ in the intermediates of formula IV and IX above represents a boronic acid moiety —B(OH)₂ or a cyclic ester thereof formed with pinacol or neopentyl glycol, the relevant compound IV or IX may be prepared by reacting bis(pinacolato)diboron or bis(neopentyl glycolato)diborane respectively with a compound of formula VI or VII as defined above; in the presence of a transition metal catalyst.

The transition metal catalyst of use in the reaction between bis(pinacolato)diboron or bis(neopentyl glycolato) diborane and compound VI or VII is suitably dichloro[1,1'-bis(diphenylphosphino)ferrocene]palladium(II). The reaction is conveniently carried out at an elevated temperature in a solvent such as 1,4-dioxane, optionally in admixture with dimethylsulfoxide, typically in the presence of 1,1'-bis (diphenylphosphino)ferrocene and/or potassium acetate.

Where $L^1$ in the intermediates of formula VII above represents triflyloxy, the relevant compound VII may be prepared by reacting the appropriate compound of formula XI as defined above with N-phenyltriflimide, typically in the presence of triethylamine; or with triflic anhydride, typically in the presence of pyridine. Analogous conditions may be utilised for compound of formula VI wherein $L^1$ represents triflyloxy from the corresponding hydroxy precursor.

The intermediates of formula XI above may suitably be prepared from the appropriate methoxy-substituted precursor of formula XIII:

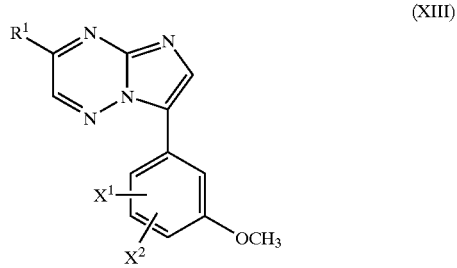

(XIII)

wherein $X^1$, $X^2$ and $R^1$ are as defined above; by treatment with boron tribromide, typically in chloroform or dichloromethane; or with hydrogen bromide, typically in acetic acid at reflux.

The intermediates of formula XII and XIII above may be prepared by reacting a compound of formula III as defined above with the appropriate compound of formula XIV:

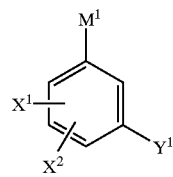

(XIV)

wherein $X^1$, $X^2$ and $M^1$ are as defined above, and $Y^1$ represents amino or methoxy; in the presence of a transition metal catalyst; under conditions analogous to those described above for the reaction between compounds III and IV. In particular, the transition metal catalyst of use in the reaction between compounds III and XIV is suitably tetrakis(triphenylphosphine)palladium(O), in which case the reaction is conveniently, carried out at an elevated temperature in a solvent such as aqueous 1,2-dimethoxyethane, advantageously in the presence of sodium carbonate.

Where $L^1$ in the intermediates of formula III above represents bromo, this compound may be prepared by bromination of the corresponding compound of formula XV:

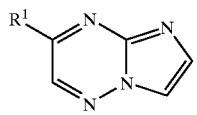

(XV)

wherein $R^1$ is as defined above; typically by treatment with bromine in acetic acid, in the presence of sodium acetate and optionally also potassium bromide.

The intermediates of formula XV may be prepared by reacting bromoacetaldehyde with the requisite compound of formula XVI:

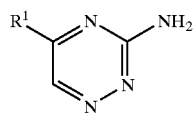

(XVI)

wherein $R^1$ is as defined above.

The reaction is conveniently carried out by heating the reactants in 1,2-dimethoxyethane, or a lower alkanol such as methanol and/or ethanol, typically at a temperature in the region of 60–80° C.

In a still further procedure, the compounds according to the present invention may be prepared by a process which comprises reacting a compound of formula XVI as defined above with a compound of formula XVII:

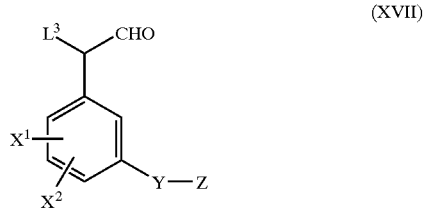

(XVII)

wherein $X^1$, $X^2$, Y and Z are as defined above, and $L^3$ represents a suitable leaving group; under conditions analogous to those described above for the reaction between bromoacetaldehyde and compound XVI.

The leaving group $L^3$ is suitably a halogen atom, e.g. bromo.

In a yet further procedure, the compounds according to the present invention wherein $R^1$ represents an aryl or heteroaryl moiety may be prepared by a process which comprises reacting a compound of formula XVIII with a compound of formula XIX:

$R^{1a}-M^1$ (XVIII)

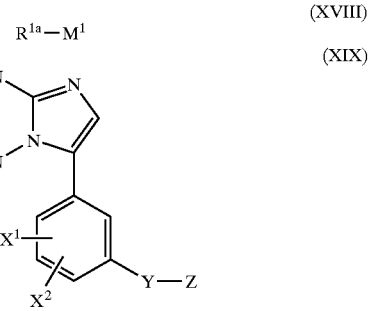

(XIX)

wherein $X^1$, $X^2$, Y, Z and $M^1$ are as defined above, $R^{1a}$ represents an aryl or heteroaryl moiety, and $L^4$ represents a suitable leaving group; in the presence of a transition metal catalyst.

The leaving group $L^4$ is typically a halogen atom, e.g chloro.

The transition metal catalyst of use in the reaction between compounds XVIII and XIX is suitably tetrakis(triphenylphosphine)palladium(O), in which case the reaction is conveniently effected at an elevated temperature in a solvent such as N,N-dimethylacetamide, typically in the presence of potassium phosphate or in the presence of lithium chloride and copper(I) iodide. Alternatively, the transition metal catalyst may suitably be tris(dibenzylideneacetone)dipalladium(O), in which case the reaction is conveniently effected at an elevated temperature in a solvent such as 1,4-dioxane, typically in the presence of tri-tert-butylphosphine and cesium carbonate.

Where $L^4$ in the compounds of formula XIX above represents a halogen atom, these compounds correspond to compounds of formula I as defined above wherein $R^1$ represents halogen, and they may therefore be prepared by any of the methods described above for the preparation of the compounds according to the invention.

The compounds according to the invention in which Y represents a chemical bond and Z represents pyrrol-1-yl may be prepared by reacting a compound of formula XII as defined above with 2,5-dimethoxytetrahydrofuran. The reaction is conveniently accomplished at an elevated temperature in a solvent such as acetic acid.

Furthermore, the compounds according to the invention may be prepared by a process which comprises reacting a compound of formula VI as defined above with a compound of formula XV as defined above in the presence of a transition metal catalyst.

The transition metal catalyst of use in the reaction between compounds VI and XV is suitably palladium(II) acetate, in which case the reaction is conveniently effected at an elevated temperature in the presence of triphenylphosphine in a solvent such as N,N-dimethylacetamide, typically in the presence of potassium acetate.

Where they are not commercially available, the starting materials of formula VI, VIII, X, XIV, XVI, XVII and XVIII may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein $R^1$ represents —C(O-Alk$^1$)$_2$R$^a$ initially obtained, wherein Alk$^1$ is $C_{1-6}$ alkyl, typically methyl or ethyl, may be converted into the corresponding compound of formula I wherein $R^1$ represents —COR$^a$ by hydrolysis with a mineral acid, typically aqueous hydrochloric acid. A compound wherein $R^1$ represents formyl may be reduced with sodium triacetoxyborohydride to the corresponding compound wherein $R^1$ represents hydroxymethyl. A compound of formula I wherein $R^1$ represents $C_{2-6}$ alkoxycarbonyl may be reduced with lithium aluminium hydride to the corresponding compound of formula I wherein $R^1$ represents hydroxymethyl. A compound of formula I wherein $R^1$ represents hydroxymethyl may be oxidised to the corresponding compound of formula I wherein $R^1$ represents formyl by treatment with manganese dioxide. The formyl derivative thereby obtained may be condensed with a hydroxylamine derivative of formula H$_2$N—OR$^b$ to provide a compound of formula I wherein $R^1$ represents —CH=NOR$^b$. Furthermore, a compound of formula I wherein $R^1$ represents —CH=NOH may be treated with triethylamine in the presence of 1,1'-carbonyldiimidazole to afford a corresponding compound of formula I wherein $R^1$ represents cyano. Alternatively, the compound of formula I wherein $R^1$ represents formyl may be reacted with a Grignard reagent of formula R$^a$MgBr to afford a compound of formula I wherein $R^1$ represents —CH(OH)R$^a$, and this compound may in turn be oxidised using manganese dioxide to the corresponding compound of formula I wherein $R^1$ represents —COR$^a$. The latter compound may then be condensed with a hydroxylamine derivative of formula H$_2$N—OR$^b$ to provide a compound of formula I wherein $R^1$ represents —CR$^a$=NOR$^b$. A compound of formula I wherein $R^1$ represents —CH(OH)R$^a$ may be converted into the corresponding compound of formula I wherein $R^{11}$ represents —CHFR$^a$ by treatment with (diethylamino)sulfur trifluoride (DAST). Similarly, a compound of formula I wherein $R^1$ represents —COR$^a$ may be converted into the corresponding compound of formula I wherein $R^1$ represents —CF$_2$R$^a$ by treatment with DAST. A compound of formula I wherein $R^1$ represents amino may be converted into the corresponding compound of formula I wherein $R^1$ represents chloro by diazotisation, using sodium nitrite, followed by treatment with copper(I) chloride. A compound of formula I wherein $R^1$ represents —COCH$_3$ may be treated with thioacetamide in the presence of pyridinium tribromide to furnish the corresponding compound of formula I wherein $R^1$ represents 2-methylthiazol-5-yl. Moreover, a compound of formula I wherein $R^1$ is formyl may be treated with (p-tolylsulfonyl)methyl isocyande (TosMIC) in the presence of potassium carbonate to afford the corresponding compound of formula I wherein $R^1$ represents oxazol-5-yl. A compound of formula I wherein $R^1$ represents hydroxymethyl may be treated with carbon tetrabromide and triphenylphosphine to afford the corresponding compound of formula I wherein $R^1$ represents bromomethyl, which may then be reacted (typically it situ) with the sodium salt of imidazole or 1H-[1,2,4]triazole to provide a compound of formula I wherein $R^1$ represents imidazol-1-ylmethyl or [1,2,4]triazol-1-ylmethyl respectively; or with the sodium salt of 1H-[1,2,3]triazole to provide a mixture of compounds of formula I wherein $R^1$ represents [1,2,3]triazol-1-ylmethyl and [1,2,3]triazol-2-ylmethyl; or with morpholine to provide a compound of formula I wherein $R^1$ represents morpholin-4-ylmethyl. A compound of formula I wherein Z is substituted with methoxy may be converted to the corresponding compound wherein Z is substituted with hydroxy by treatment with boron tribromide. Moreover, a compound of formula I wherein $X^1$ represents $C_{1-6}$ alkoxy, e.g. methoxy, may be converted into the corresponding compound of formula I wherein $X^1$ represents hydroxy by treatment with boron tribromide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 and/or α3 and/or α5 subunit stably expressed in Ltk⁻ cells.

Reagents
Phosphate buffered saline (PBS).
Assay buffer: 10 mM $KH_2PO_4$, 100 mM KCl, pH 7.4 at room temperature.
[$^3$H]-Flumazenil (18 nM for $\alpha1\beta3\gamma2$ cells; 18 nM for $\alpha2\beta3\gamma2$ cells; 10 nM for $\alpha3\beta3\gamma2$ cells; 10 nM for $\alpha5\beta3\gamma2$ cells) in assay buffer.
Flunitrazepam 100 µM in assay buffer.
Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:
300 µl of assay buffer.
50 µl of [$^3$H]-flumazenil (final concentration for $\alpha1\beta3\gamma2$: 1.8 nM; for $\alpha2\beta3\gamma2$: 1.8 nM; for $\alpha3\beta3\gamma2$: 1.0 nM; for $\alpha5\beta3\gamma2$: 1.0 nM).
50 µl of buffer or solvent carrier (e.g. 10% DMSO) if compounds are dissolved in 10% DMSO (total); test compound or flunitrazepam (to determine non-specific binding), 10 µM final concentration.
100 µl of cells.

Assays are incubated for 1 hour at 40° C. then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the $\alpha2$ and/or $\alpha3$ and/or $\alpha5$ subunit of the human $GABA_A$ receptor of 100 nM or less.

EXAMPLE 1

2-{7-[2,4-Difluoro-3-(pyridin-4-yl)phenyl]imidazo[1,2-b][1,2,4]triazin-3-yl}propan-2-ol a) 1,1-Dibromo-3-hydroxy-3-methylbutan-2-one To a stirred solution of 3-methyl-3-hydroxy-2-butanone (40 g, 0.392 mol) in anhydrous dichloromethane (2.2 l) under nitrogen was added solid pyridinium tribromide (250.4 g, 0.784 mol) in portions and the mixture was stirred at room temperature for 14 h. The mixture was then washed with dilute aqueous sodium hydrogensulphite (500 ml), then saturated aqueous NaCl (500 ml), dried ($Na_2SO_4$), and evaporated in vacuo. The residue was purified by flash chromatography (silica gel, $CH_2Cl_2$) to afford 31.4 g (31%) of the title compound as a colourless oil: $^1$H NMR (360 MHz, $CDCl_3$) δ 1.54 (6H, s), 2.45 (1H, br s), 6.62 (1H, s).

b) 2-(3-Amino-[1,2,4]triazin-5-yl)propan-2-ol and 2-(3-Amino-[1,2,4]triazin-6-yl)propan-2-ol To a stirred solution of sodium acetate trihydrate (32.9 g, 0.342 mol) in water (90 ml) was added 1,1-dibromo-3-hydroxy-3-methylbutan-2-one (29.6 g, 0.114 mol). The solution was heated at reflux under nitrogen for 30 min, then allowed to cool to room temperature before adding solid aminoguanidine bicarbonate (15.54 g, 0.114 mol). The resulting pale yellow solution (pH 5) was stirred at room temperature for 15 min, then 4 N aqueous NaOH solution (56.9 ml, 0.228 mol) was added and the mixture (pH 10) was stirred under nitrogen for a further 14 h. The solution was continuously extracted with warm dichloromethane over a period of 24 h. After this time the solvent was evaporated to leave a residue which was triturated with diethyl ether to give a solid. The solid was collected by filtration and dried at 60° C. under vacuum to give 8.17 g (47%) of a mixture of two isomers in a 60:40 ratio with the required 2-(3-amino-[1,2,4]triazin-5-yl)propan-2-ol being the major product: $^1$H NMR (360 MHz, DMSO-$d_6$) δ 1.38 (major) and 1.47 (minor) (6H, s), 5.30 (major) and 5.43 (minor) (1H, br s), 7.01 (major) and 7.06 (minor) (2H, br s), 8.43 (major) and 8.80 (minor) (1H, s); MS (ES$^+$) m/z 155 [M+H]$^+$.

c) 2-(Imidazo[1 2-b][1,2,4]triazin-3-yl)pronan-2-ol

A stirred mixture of bromoacetaldehyde diethyl acetal (16.5 ml, 0.106 mol) in concentrated hydrobromic acid (4.13 ml) and water (4.13 ml) was heated at reflux for 40 min, then poured into ethanol (175 ml). The solution was neutralised to pH 7 with solid sodium hydrogencarbonate, then filtered, washing the solid with more ethanol (30 ml). To the filtrate was added a 60:40 mixture of 2-(3-amino-[1,2,4]triazin-5-yl)propan-2-ol and 2-(3-amino-[1,2,4]triazin-6-yl)propan-2-ol (8.17 g, 0.053 mol) and the mixture was stirred at reflux temperature for 6 h. The mixture was evaporated in vacuo, and the residue was triturated with hot dichloromethane and filtered. The solid was triturated with hot acetone and collected bid filtration again to leave a white solid (14 g). The solid was dissolved in water (30 ml) and continuously extracted with hot dichloromethane over a period of 24 h. The organic layer was separated and concentrated under vacuum to leave a thick yellow oil (3 g) which favoured the required isomer in a ratio of 4:1. The required product was obtained in pure form by flash chromatography (silica gel, 2% MeOH/$CH_2Cl_2$) to give 2.12 g (23%) of the title compound as a pale yellow solid: $^1$H NMR (360 MHz, $CDCl_3$) δ 1.69 (6H, s), 3.69 (1H, br s), 7.93 (2H, s), 8.70 (1H, s).

d) 2-(7-Bromoimidazo[1,2-b][1,2,4]triazin-3-yl)propan-2-ol

To a stirred solution of 2-(imidazo[1,2-b][1,2,4]triazin-3-yl)propan-2-ol (5.55 g, 31.1 mmol) in acetic acid (100 ml) was added sodium acetate (3.83 g, 46.7 mmol), then, dropwise over 5 min, a solution of bromine (1.77 ml, 34.4 mmol) in acetic acid (12 ml). The solution was stirred at room temperature for 25 min, then partitioned between saturated aqueous $NaHCO_3$ (2 l) and ethyl acetate (1 l). The aqueous layer (pH 7) was further extracted with ethyl acetate (1 l), and the combined organic extracts were dried ($Na_2SO_4$) and evaporated in vacuo. The residue was purified by flash chromatography (silica gel, 2% MeOH/CH$_2$Cl$_2$) to afford 6.17 g (77%) of the title compound as a yellow solid: $^1$H NMR (360 MHz, CDCl$_3$) δ 1.70 (6H, s), 3.12 (1H, br s), 7.95 (1H, s), 8.80 (1H, s).

e) 2-{7-[2,4-Difluoro-3-(pyridin-4-yl)phenyl]imidazo[1,2-b][1,2,4]triazin-3-yl}propan-2ol A suspension of 4-bromopyridine hydrochloride (6.81 g, 35 mmol) in tetrahydrofuran (100 ml) was treated with sodium hydroxide (8.75 ml of a 4 N solution in water) and this mixture was stirred at ambient temperature for 5 min. 2,6-Difluorobenzeneboronic acid (6.36 g, 40 mmol) and potassium fluoride (6.71 g, 116 mmol) were added and this mixture was degassed with nitrogen for 10 min before adding tris(dibenzylideneacetone)dipalladium(0) (640 mg, 0.7 mmol) followed by tri-tert-butylphosphine (7 ml of a 0.2 M solution in 1,4-dioxane, 1.4 mmol). This mixture was stirred at ambient temperature for 15 min then heated at 50° C. for 30 min. The reaction mixture was diluted with dichloromethane then extracted with ice-cold 1 N sodium hydroxide solution (×2). The organics were dried over anhydrous magnesium sulphate, filtered and pre-adsorbed onto silica. Purification by chromatography (silica gel, 20–30% EtOAc/isohexane containing 0.5% methanol and 0.5% triethylamine) gave 4-(2,6-difluorophenyl)pyridine as a white solid (3.2 g, 48%): $^1$H NMR (360 MHz, CDCl$_3$) δ 6.99–7.06 (2H, m), 7.32–7.39 (1H, m), 7.40–7.42 (2H, m), 8.71 (2H, d, J 6).

A solution of 2,2,6,6-tetramethylpiperidine (3.10 ml, 18.4 mmol) in THF (80 ml) was cooled to −20° C., then treated with a 2.5 M solution of butyllithium in hexanes (7.03 ml, 17.6 mmol). After stirring at −20° C. for 10 min, the mixture was cooled to −78° C. and treated with a solution of 4-(2,6-difluorophenyl)pyridine (3.20 g, 16.7 mmol) in THF (20 ml). The mixture was stirred at −78° C. for 1.5 h before adding trimethyl borate (3.78 ml, 33.5 mmol). The mixture was allowed to warm to room temperature before adding 5 N aqueous HCl (20 ml). After stirring for 12 h, the solvent was removed in vacuo and the residue was partitioned between 1 N aqueous HCl (100 ml) and diethyl ether (100 ml). The organic layer was then extracted with 1 N aqueous NaOH and the aqueous layer was acidified to pH 8 with 5 N aqueous HCl. The resulting solid was collected by filtration, washed with water and dried to afford 3.20 g (81%) of 2,4-difluoro-3-(pyridin-4-yl)benzeneboronic acid as a white solid: MS (ES$^+$) m/z 235 [M+H]$^+$.

A mixture of 2-(7-bromoimidazo[1,2-b][1,2,4]triazin-3-yl)propan-2-ol (0.10 g, 0.38 mmol), 2,4-difluoro-3-(pyridin-4-yl)benzeneboronic acid (0.14 g, 0.58 mmol) and sodium carbonate (950 μL of a 2 M solution) in ethylene glycol dimethyl ether (2 ml) was degassed by bubbling nitrogen through for 20 min. Tetrakis(triphenylphosphine)palladium (0) (0.02 g, 0.02 mmol) was added and the mixture was degassed for a further 20 min before heating at 80° C. for 18 h. The mixture was filtered through glass fibre paper, and partitioned between ethyl acetate (30 ml) and water (30 ml). The organic layer was dried (Na$_2$SO$_4$), filtered and evaporated in vacuo. Purification by chromatography (silica gel, 5% MeOH/CH$_2$C$_{12}$), then recrystallisation from EtOAc/CH$_2$C$_{12}$, gave 7.0 mg (5%) of the title compound: $^1$H NMR (360 MHz, CDCl$_3$) δ 7.19–7.24 (1H, s), 7.47 (2H, d, J 4.6), 8.14–8.21 (1H, m), 8.28 (1H, d, J 2.5), 8.77 (3H, dd, J 4.6, 6.0).

EXAMPLE 2

3'-[3-(1-Hydroxy-1-methylethyl)imidazo[1,2-b][1,2,4]triazin-7-yl]-6,2',6'-trifluorobiphenyl-2-carbonitrile a)
3-Fluoro-2-(4,4,5,5-tetramethyl-[1,3,2]dioxaborolan-2-yl)benzonitrile A mixture of 2,3-difluorobenzonitrile (19.0 g, 137 mmol) and ethanol (200 ml) pre-saturated with ammonia gas was heated at 140° C. in an autoclave for 8 h (terminal pressure 200 psi). The mixture was allowed to cool to ambient temperature and evaporated to dryness. The residue was dissolved in water (400 ml) and extracted with diethyl ether (2×300 ml). The combined organics were washed with water (300 ml) and brine (250 ml), dried over anhydrous magnesium sulfate, filtered and evaporated. Trituration with isohexane (150 ml) afforded 2-amino-3-fluorobenzonitrile (9.8 g, 50%) as an off-white solid: $^1$H NMR (360 MHz, CDCl$_3$) δ 4.47 (2H, s), 6.65–6.71 (1H, m), 7.14–7.20 (2H, m).

To a solution of 2-amino-3-fluorobenzonitrile (17.07 g, 0.125 mol) in 1,4-dioxane (20 ml) was added 48% aqueous hydrobromic acid (200 ml) and the solution was cooled to 0° C. before adding dropwise a solution of sodium nitrite (9.95 g, 0.144 mol) in water (22 ml) over 35 min so that the temperature did not rise above 3° C. The resulting mixture was stirred at 2–3° C. for 2 h then poured onto a cooled (5° C.) solution of copper(I) bromide (26.98 g, 0.188 mol) in 48% hydrobromic acid (100 ml). The mixture was stirred for 10 min then heated to 50° C. over 1 h. The mixture was cooled to ambient temperature, diluted with water (1 l) and extracted with diethyl ether (2×500 ml). The combined organic extracts were washed with 1 M aqueous Na$_2$SO$_3$ (500 ml), then saturated aqueous NH$_4$Cl (200 ml), dried (MgSO$_4$), and evaporated to give a brown oil/solid. Purification by chromatography (silica gel, 10% EtOAc/isohexane) and trituration of a mixed fraction with isohexane afforded 13.22 g (53%) of 2-bromo-3-fluorobenzonitrile as a pale yellow solid: $^1$H NMR (360 MHz, CDCl$_3$) δ 7.62–7.68 (1H, m), 7.74–7.85 (1H, ddd, J 9, 9, 1), 7.74–7.85 (1H, ddd, J 8, 1, 1).

A mixture of 2-bromo-3-fluorobenzonitrile (1.20 g, 6.00 mmol), dried potassium acetate (1.18 g, 12.0 mmol) and bis(pinacolato)diboron (1.75 g, 6.89 mmol) in 1,4-dioxane (14.7 ml) and dimethylsulfoxide (0.3 ml) was degassed by bubbling nitrogen through the mixture for 50 min. Dichloro [1,1'-bis(diphenylphosphino)ferrocene]palladium(II) dichloromethane adduct (0.1481 g, 0.181 mmol) was added and the mixture was degassed for a further 10 min, then heated at 90° C. under nitrogen for 18 h. After allowing to cool, the mixture was filtered through glass fibre paper, and the solid was washed with a little dichloromethane. The combined filtrates were evaporated in vacuo and the residue was partitioned between 2 M aqueous NaOH (21 ml) and diethyl ether (20 ml). The aqueous layer was then acidified to pH 5 with concentrated hydrochloric acid (3 ml), causing a solid to precipitate. After leaving in a fridge for 3 days, the solid was collected by filtration, washed with water and dried under vacuum to leave 0.9191 g (62%) of the title compound as a white solid: $^1$H NMR (360 MHz, DMSO-d$_6$) δ 1.34 (12H, s), 7.55–7.59 (1H, mn), 7.69–7.75 (2H, m).

b) 3-Bromo-2,4-difluorophenylamine

A mixture of 2,6-difluorobromobenzene (125.5 g, 650 mmol) in 98% sulphuric acid (250 ml) was cooled in an ice-water bath and then treated with a 1:1 mixture of 98% sulphuric acid and fuming nitric acid (100 ml) added at such a rate that the internal temperature never exceeded 35° C. Once addition was complete the reaction was stirred at ambient temperature for 3 h then poured onto ice. This mixture was diluted with water (final volume 5 l), the resulting solid collected by filtration, washed with water, then dried under vacuum over phosphorus pentoxide, to afford 2-bromo-1,3-difluoro-4-nitrobenzene as a cream-coloured solid (145 g, 94%): $^1$H NMR (360 MHz, CDCl$_3$) δ 7.10–7.15 (1H, m), 8.09–8.16 (1H, m).

A mixture of 2-bromo-1,3-difluoro-4-nitrobenzene (30 g, 130 mmol) and tin(II) chloride dihydrate in 36% hydrochloric acid (150 ml) was heated to 40° C. Diethyl ether (20 ml) was slowly added to bring about solution. Once in solution the reaction proceeded rapidly and the ether boiled away. After heating at 60° C. for 1 h the reaction was cooled and then poured onto ice-water (1.5 l). The solution was made basic (pH 13) with 30% aq. sodium hydroxide keeping the internal temperature below 20° C. The resulting grey slurry was swirled with chloroform (2×500 ml), the organic extracts were combined, washed with water, dried over an-hydrous magnesium sulfate containing 2 g decolourising charcoal, filtered and evaporated to dryness. Trituration with isohexane afforded 23 g (83%) of the title compound as a buff-coloured solid: $^1$H NMR (360 MHz, CDCl$_3$) δ 3.51 (2H, br), 6.65–6.70 (1H, mn), 6.75-6-80 (1H, m).

c) 3'-Amino-6,2',6'- trifluorobiphenyl-2-carbonitrile

A mixture of 3-bromo-2,4-difluorophenylamine (0.6451 g, 3.10 mmol) and 3-fluoro-2-(4,4,5,5-tetramethyl-[1,3,2] dioxaborolan-2-yl)benzonitrile (0.915 g, 3.70 mmol) and potassium fluoride (0.5953 g, 10.2 mmol) in tetrahydrofuran (8 ml) was degassed with nitrogen for 15 min before adding tris(dibenzylideneacetone)dipalladium(0) (56.9 mg, 0.0621 mmol) and tri-tert-butylphosphine (1.24 ml of a 0.1 M solution in 1,4-dioxane, 0.124 mmol). The mixture was degassed for a further 5 min, then heated at 50° C. for 18 h under nitrogen. After cooling to ambient temperature, the mixture was partitioned between water (50 ml) and ethyl acetate (40 ml). The organic layer was washed with saturated aqueous NaCl (20 ml), dried (Na$_2$SO$_4$) and evaporated in vacuo. The residue was purified by chromatography (silica gel, 30% EtOAc/isohexane) to afford 0.5180 g (67%) of the title compound as a yellow solid: $^1$H NMR (360 MHz, CDCl$_3$) δ 3.70 (2H, br s), 6.84–6.92 (2H, m), 7.44 (1H, t, J 8.4), 7.53 (1H, td, J 8.2, 5.1), 7.61 (1H, d, J 7.3).

d) 3'-(5,5-Dimethyl-[1,3,2]dioxaborolan-2-yl)-6,2',6'-trifluorobiphenyl-2-carbonitrile To a solution of 3'-amino-6,2',6'-trifluorobiphenyl-2-carbonitrile (0.5136 g, 2.07 mmol) in hot 1,4dioxane (1 ml) was added 48% aqueous hydrobromic acid (7 ml) and the mixture was cooled to −5° C. before adding dropwise a solution of sodium nitrite (0.1657 g, 2.40 mmol) in water (0.5 ml) over 5 min so that the temperature did not rise above −4° C. The resulting mixture was stirred at −5 to 2° C. for 2 h before adding a cooled (5° C.) solution of copper(I) bromide (0.4452 g, 3.10 mmol) in 48% hydrobromic acid (3 ml). The mixture was stirred for 5 min then heated to 46° C. over 1 h. The mixture was cooled to ambient temperature, diluted with water (50 ml) and extracted with diethyl ether (2×30 ml). The combined organic extracts were washed with 10% aqueous ammonia (25 ml), then saturated aqueous NaCl (20 ml), dried (MgSO$_4$), and evaporated in vacuo. Purification by chromatography (silica gel, 20% EtOAc/isohexane) gave 0.3790 g (59%) of 3'-bromo-6,2',6'-trifluorobiphenyl-2-carbonitrile as a white solid.

A mixture of 3'-bromo-6,2',6'-trifluorobiphenyl-2-carbonitrile (0.3745 g, 1.20 mmol), dried potassium acetate (0.2327 g, 2.37 mmol) and bis(neopentyl glycolato)diboron (0.3529 g, 1.56 mmol) in 1,4-dioxane (9.8 ml) and dimethylsulfoxide (0.2 ml) was degassed by bubbling nitrogen through the mixture for 1 h. Dichloro[1,1'-bis(diphenylphosphino)-ferrocene]palladium(II) dichloromethane adduct (30.0 mg, 0.037 mmol) was added and the mixture was heated at 85° C. under nitrogen for 18 h. After allowing to cool, the mixture was diluted with diethyl ether (10 ml), filtered through glass fibre paper, and the solid was washed with diethyl ether. The combined filtrates were evaporated in vacuo and the residue was dissolved in diethyl ether (20 ml) and extracted with 1 N aqueous NaOH (2×20 ml). The combined aqueous extracts were then acidified to pH 5 with concentrated hydrochloric acid and extracted with diethyl ether (2×20 ml). The combined organic extracts were washed with saturated aqueous NaCl (10 ml), dried (MgSO$_4$) and evaporated in vacuo to afford 0.2401 g (57%) of the title compound as a brown oil: $^1$H NMR (360 MHz, CDCl$_3$) δ 1.04 (6H, s), 3.79 (4H, s), 7.04(1H, t, J 8.8), 7.42 (1H, td, J 8.8, 1.1), 7.52 (1H, td, J 8.4, 4.9), 7.59(1H, dd, J 7.7, 1.1), 7.88(1H, dt, J 8.4, 7.0).

e) 3'-[3-(1-Hydroxy-1-methylethyl)imidazo[1,2-b] [1,2,4]triazini-7-yl]-6,2',6'trifluorobiphenyl-2-carbonitrile A mixture of 2- (7-bromoimidazo[1,2-b][1,2,4]triazin-3-yl)propan-2-ol (from Example 11 step d) (0.131 g, 0.510 mmol), 3'-(5,5-dimethyl-[1,3,2]dioxaborolan-2-yl)-6,2',6'-trifluorobiphenyl-2-carbonitrile (0.2311 g, 0.663 mmol) and sodium carbonate (663 μl of a 2 M solution, 1.33 mmol) in ethylene glycol dimethyl ether (3 ml) was degassed by bubbling nitrogen through for 15 min. Tetrakis(triphenylphosphine)palladium(0) (0.0297 g, 0.0257 mmol) was added and the mixture was heated at 80° C. for 18 h. The mixture was partitioned between ethyl acetate (25 ml) and water (10 ml). The aqueous layer was extracted further with ethyl acetate (25 ml), and the combined organic extracts were dried (Na$_2$SO$_4$), filtered and evaporated in vacuo. Purification by chromatography (silica gel, 50% EtOAc/isohexane) gave 95.5 mg (46%) of the title compound as a yellow solid: mp 177–179° C. (EtOAc-isohexane); 1H NMR (360 MHz, CDCl$_3$) δ 1.72 (6H, s), 3.35 (1H, s), 7.26 (1H, td, J 8.3, 1.5), 7.50 (1H, td, J 8.2, 1.2), 7.60 (1H, td, J 8.2, 5.1), 7.67 (1H, dd, J 7.8, 1.6), 8.31 (1H, d, J 3.1), 8.34 (1H, dt, J 8.6, 5.9), 8.80 (1H, s); MS (ES$^+$) m/z 410 [M+H]$^+$. Anal. Found: C, 61.23; H, 3.44; N, 16.73%. Required for C$_{21}$H$_{14}$F$_3$N$_5$O: C, 61.61; H, 3.44; N, 17.11%.

EXAMPLE 3

3'-[3-(1-Fluoro-1-methylethyl)imidazo[1,2-b][1,2,4]triazin-7-yl]-4,2',6'-trifluorobiphenyl-2-carbonitrile a) 3-Methyl-3-fluoro-2-butanone This was prepared from 3-bromo-3-methyl-2-butanone as described by Fry and Migron (*Tetrahedron Lett.*, 1979, 3357–3360) to give, after distillation using a Vigreux column, a 47% yield of a 94:6 mixture of the title compound and 3-methyl-3-buten-2-one as a colourless oil: bp 74–6° C.; $^1$H NMR (360 MHz, CDCl$_3$) δ 1.45 (6H, d, J 21.5), 2.28 (3H, d, J 5.0).

b) ,1-Dibromo-3-fluoro-3-methylbutan-2-one

To a stirred solution of 3-methyl-3-fluoro-2-butanone (0.1031 g, 0.990 mmol) in anhydrous dichloromethane (5 ml) under nitrogen was added solid pyridinium tribromide (0.7035 g, 1.98 mmol) and the mixture was stirred at room temperature for 18 h. The mixture was then diluted with dichloromethane (5 ml), washed with dilute aqueous sodium hydrogensulfite (10 ml), then saturated aqueous NaCl (10 ml), dried ($Na_2SO_4$) and evaporated under low vacuum with no heat. The residue was purified by flash chromatography [silica gel, 5% $Et_2O$/petroleum ether (40–60° C.)] to afford 0.1869 g (72%) of the title compound as a colourless oil: $^1$H NMR (360 MHz, $CDCl_3$) δ 1.65 (6H, d, J 21.5), 6.51 (1H, d, J 1.5).

c) 3-Amino-5-(1-fluoro-1-methylethyl)-1,2,4-triazine

A stirred solution of sodium acetate trihydrate (23.07 g, 80.7 mmol) and 1,1-dibromo-3-fluoro-3-methylbutan-2-one (21.14 g, 80.7 mmol) in water (80 ml) was heated at reflux under nitrogen for 40 min, then allowed to cool to room temperature before adding solid aminoguanidine bicarbonate (10.99 g, 80.7 mmol). The mixture was stirred at room temperature for 5 h, then 4 N aqueous NaOH solution (40.4 ml, 162 mmol) was added and the mixture was stirred under nitrogen for a further 3 days. The mixture was filtered and the solid was washed with water twice, then dried under vacuum at 60° C. to give 6.40 g (51%) of the title compound as a yellow-brown solid: $^1$H NMR (360 MHz, DMSO-$d_6$) δ 1.63 (6H, d, J 22.2), 7.32 (2H, br s), 8.73 (1H, d, J 1.0); MS ($ES^+$) m/z 157 $[M+H]^+$.

d) 3-(1-Fluoro-1-methylethyl)imidazo[1,2-b][1,2,4]triazine

A stirred mixture of bromoacetaldehyde diethyl acetal (1.20 ml, 7.73 mmol) in concentrated hydrobromic acid (0.38 ml) and water (0.38 ml) was heated at reflux for 40 min, then poured into ethanol (3 ml). The solution was neutralised to pH 7 with solid sodium hydrogencarbonate, then filtered, washing the solid with more ethanol (3 ml). To the filtrate was added 3-amino-5-(1-fluoro-1-methylethyl)-1,2,4-triazine (1.0046 g, 6.43 mmol) and the mixture was stirred at 70–80° C. for 17 h. The mixture was evaporated in vacuo, and the residue was purified by flash chromatography (silica gel, 70% EtOAc/isohexane to 15% MeOH/EtOAc, then 20% EtOAc/$CH_2Cl_2$) to give 0.2000 g (17%) of the title compound as a pale yellow solid: $^1$H NMR (360 MHz, $CDCl_3$) δ 1.82 (6H, d, J 22 1), 7.97 (1H, d, J 1.3), 7.99 (1H, d, J 1.2), 8.69 (1H, d, J 1.0).

e) 7-Bromo-3-(1-fluoro-1-methylethyl)imidazo[1,2-b][1,2,4]triazine

To a stirred solution of 3-(1-fluoro-1-methylethyl)imidazo[1,2-b][1,2,4]triazine (0.6208 g, 3.45 mmol) in acetic acid (15 ml) was added sodium acetate (0.4251 g, 5.18 mmol), then, dropwise over 5 min, a solution of bromine (0.195 ml, 3.78 mmol) in acetic acid (2 ml). The solution was stirred at room temperature for 30 min, then partitioned between saturated aqueous $NaHCO_3$ (300 ml) and ethyl acetate (150 ml). The aqueous layer (pH 7) was further extracted with ethyl acetate (2×150 ml), and the combined organic extracts were dried ($Na_2SO_4$) and evaporated in vacuo. The residue was purified by flash chromatography (silica gel, 25% EtOAc/isohexane) to afford 0.8437 g (95%) of the title compound as a yellow solid: $^1$H NMR (360 MHz, $CDCl_3$) δ 1.82 (6H, d, J 22.1), 7.99 (1H, s), 8.81 (1H, d, J 1.1).

f) 3'-[3-(1-Fluoro-1-methylethyl)imidazo[1,2-b][1,2,4]triazin-7-yl]-4,2',6'-trifluorobiphenyl-2-carbonitrile 2-Bromo-5-fluorobenzonitrile was converted to 5-fluoro-2-(4,4,5,5-tetramethyl-[1,3,2]dioxaborolan-2-yl)benzonitrile using a similar procedure to that described in Example 2, step a, to give a straw-coloured solid: $^1$H: NMR (360 MHz, $CDCl_3$) δ 1.38 (12H, s), 7.27 (1H, ddd, J 8, 8.2), 7.39 (1H, dd, J 9, 2), 7.90 (1H, dd, J 8, 6).

A solution of 3-bromo-2,4-difluorophenylamine (from Example 2, step b) (5.2 g, 25 mmol) and 5-fluoro-2-(4,4,5,5-tetramethyl-[1,3,2]dioxaborolan-2-yl)benzonitrile (7.10 g, 28.8 mmol) in tetrahydrofuran (95 ml) and water (5 ml) was treated with potassium fluoride (4.8 g, 82.5 mmol) and this mixture was degassed with nitrogen for 10 min before adding tris(dibenzylideneacetone)dipalladium(0) (460 mg, 0.5 mmol) and tri-tert-butylphosphine (2.5 ml of a 0.2 M solution in 1,4-dioxane, 0.5 mmol). The reaction was then heated at 50° C. for 2 h then cooled to ambient temperature. The mixture was poured into ice-cold 0.5 N sodium hydroxide (750 ml), stirred for 10 min and the solid collected by filtration. This was triturated with water and dried to afford 3'-amino-4,2',6'-trifluorobiphenyl-2-carbonitrile as a grey powder (6.6 g), which was used without further purification: $^1$H NMR (360 MHz, $CDCl_3$) δ 3.74 (2H, br s), 6.79–6.89 (2H, m), 7.36–7.42 (1H, m), 7.45–7.51 (2H, m).

3'-Amino-4,2',6'-trifluorobiphenyl-2-carbonitrile was bromo-deaminated by a similar procedure to that described in Example 2, step a, to give 3'-bromo-4,2',6'-trifluorobiphenyl-2-carbonitrile in 92% yield as an orange solid: $^1$H NMR (360 MHz, $CDCl_3$) δ 6.97–7.03 (1H, m), 7.39–7.54 (3H, m), 7.62–7.68 (1H, m).

3'-Bromo-4,2',6'-trifluorobiphenyl-2-carbonitrile was reacted with bis(pinacolato)diboron by a similar procedure to that described in Example 2, step a, to give 3'-(4,4,5,5-tetramethyl-[1,3,2]dioxaborolan-2-yl)-4,2',6'-trifluorobiphenyl-2-carbonitrile in 63% yield as a buff-coloured solid: MS ($ES^+$) m/z 360 $[M+H]^+$.

3'-(4,4,5,5-Tetramethyl-[1,3,2]dioxaborolan-2-yl)-4,2',6'-trifluorobiphenyl-2-carbonitrile was reacted with 7-bromo-3-(1-fluoro-1-methylethyl)imidazo[1,2-b][1,2,4]triazine by a similar procedure to that described in Example 2, step e, to give the title compound in 38% yield as a yellow solid: mp 166-169° C. (EtOAc-isohexane); $^1$H NMR (360 MHz, $CDCl_3$) δ 1.85 (6H, d, J 22.1); 7.25 (1H, td, J 8.6, 1.4), 7.46 (1H, td, J 8.6, 2.7), 7.54–7.59 (2H, m), 8.30 (1H, dt, J 8.3, 6.2), 8.35 (1H, d, J 3.0), 8.80 (1H, d, J 1.2); MS ($ES^+$) m/z 412 $[M+H]^+$. Anal. Found: C, 61.34; H, 3.29; N, 16.72%. Required for $C_{21}H_{13}F_4N_5 \cdot 0.05C_4H_8O_2$: C, 61.24; H, 3.25; N, 16.84%.

EXAMPLE 4

7-[2,4-Difluoro-3-(pyridin-3-yl)phenyl]-3-trifluoromethylimidazo[1,2-b][1,2,4]triazine a) 3-Amino-5-trifluoromethyl-1,2,4-triazine

To a stirred solution of sodium acetate trihydrate (22.62 g, 166.2 mmol) in water (80 ml) was added 1,1-dibromo-3,3,3-trifluoroacetone (21.57 g, 79.9 mmol). The solution was heated at reflux under nitrogen for 30 min, then allowed to cool to room temperature before adding solid aminoguanidine bicarbonate (10.88 g, 79.9 mmol). The resulting pale yellow solution (pH 5) was stirred at room temperature for 3 h, then 4 N aqueous NaOH solution (40 ml, 160 mmol) was added causing a precipitate to appear. The mixture (pH 10) was stirred under nitrogen for a further 39 h. The solid was collected by filtration, washed with water and dried at 60° C. under vacuum to give 6.96 g of a mixture of two isomers in a 28:72 ratio. This was further purified by flash chromatography (silica gel, 30% EtOAc/isohexane), then recrystallised from ethanol to afford 3.53 g (27%) of the title compound: $^1$H NMR (400 MHz, DMSO-$d_6$) δ 8.00 (2H, br s), 9.08 (1H, s).

b) 3-Trifluoromethylimidazo[1,2-b][1,2,4]triazine

A stirred mixture of bromoacetaldehyde diethyl acetal (2.30 ml, 14.8 mmol) in concentrated hydrobromic acid (0.73 ml) and water (0.73 ml) was heated at reflux for 2 h, then poured into ethanol (25 ml). The solution was neutralised to pH 7 with solid sodium hydrogencarbonate, then filtered. To the filtrate was added 3-amino-5-trifluoromethyl-1,2,4-triazine (1.0079 g, 6.14 mmol) and the mixture was stirred at 60° C. for 20 h, then 80° C. for 23 h. The mixture was evaporated in vacuo, and the residue was purified by flash chromatography (silica gel, 35-50% EtOAc/isohexane) to give 0.2593 g (22%) of the title compound: $^1$H NMR (360 MHz, CDCl$_3$) δ 8.20 (1H, d, J0.8), 8.30 (1H, d, J 0.9), 8.73 (1H, s).

c) 7-Bromo-3-trifluoromethylimidazo[1,2-b][1,2,4]triazine

To a solution of 3-trifluoromethylimidazo[1,2-b][1,2,4]triazine (0.2211 g, 1.18 mmol) in acetic acid (6 ml) was added sodium acetate (0.1470 g, 1.79 mmol), then bromine (90.8 µl, 1.76 mmol). The solution was stirred at room temperature for 6 h, then partitioned between saturated aqueous NaHCO$_3$ (100 ml) and ethyl acetate (100 ml). The aqueous layer (pH 9) was further extracted with ethyl acetate (100 ml), and the combined organic extracts were dried (Na$_2$SO$_4$) and evaporated in vacuo. The residue was purified by flash chromatography (silica gel, 25% EtOAc/isohexane) to afford 0.2073 g (66%) of the title compound: 1H NMR (360 MHz, CDCl$_3$) δ 8.30 (1H, s), 8.83 (1H, s).

d) 2,4-Difluoro-3-(pyridin-3-yl)phenylamine

A mixture of 3-bromo-2,4-difluorophenylamine (from Example 2, step b) (12.5 g, 60 mmol), diethyl(3-pyridyl)borane (10.6 g, 72 mmol) and potassium carbonate (16.6 g, 120 mmol) in tetrahydrofuran (150 ml) and water (50 ml) was degassed with nitrogen for 15 min. To this mixture was added tetrakis(triphenylphosphine)palladium(0) (2.1 g, 1.8 mmol) and the reaction was heated at reflux for 4 days. The mixture was cooled to ambient temperature and the majority of the tetrahydrofuran removed on a rotary evaporator. The residue was diluted with water (250 ml), extracted with ethyl acetate (300 ml), the organics were washed with water, brine, dried over anhydrous magnesium sulfate, filtered and pre-adsorbed onto silica. Purification by chromatography [silica gel, 10–50% EtOAc/isohexane (containing 1% triethylamine)] afforded 5.8 g (47%) of the title compound as a cream-coloured solid: 1H NMR (400 MHz, CDCl$_3$) δ 3.69 (2H, br s), 6.72–6.88 (2H, m), 7.39 (1H, dd, J 8, 5), 7.80 (1H, d, J 8), 8.62 (1H, dd, J 5, 1), 8.72 (1H, s).

e) 3-(3-Bromo-2,6-difluorophenyl)pyridine

A warm solution of 2,4-difluoro-3-pyridin-3-yl)phenylamine (5.80 g, 28.1 mmol) in 1,4-dioxane (10 ml) was treated with a solution of 48% aqueous hydrobromic acid (100 ml). The resulting suspension was cooled to 0° C. before being treated dropwise over 45 min with a solution of sodium nitrite (2.23 g, 32.3 mmol) in water (5 ml). After stirring at 0° C. for 2 h, a cooled (0° C.) solution of copper(I) bromide (12.11 g, 84.4 mmol) in 48% aqueous hydrobromic acid (50 ml) was added to the reaction which was stirred at 0° C. for 10 min then heated at 50° C. for 20 min. The reaction was cooled to ambient temperature, poured onto ice-cold conc. ammonia (500 ml) and the product was extracted into ethyl acetate (2×400 ml). The organics were washed with water (200 ml) and brine (200 ml), dried over anhydrous sodium sulfate, filtered and concentrated in vacuo to give a dark oil. Purification by dry flash column chromatography [silica gel, 10%–30% EtOAc/isohexane (with 1% triethylamine and 1% methanol)] gave 4.9 g (65%) of the title compound as a pink solid: 1H NMR (400 MHz, CDCl$_3$) δ 6.97 (1H, ddd, J 9, 9, 2), 7.40–7.44 (1H, m), 7.55–7.60 (1H, m), 7.77–7.81 (1H, m), 8.66 (1H, dd, J 5, 2), 8.71 (1H, s).

f) 2,4-Difluoro-3-(pyridin-3-yl)benzeneboronic acid

A mixture of 3-(3-bromo-2,6-difluorophenyl)pyridine (2.97 g, 11 mmol), potassium acetate (2.16 g, 22 mmol) and bis(neopentyl glycolato)diboron (2.86 g, 12.7 mmol) in 1,4-dioxane (30 ml) was heated at 90° C. for 16 h. The reaction was cooled, filtered (washing the filter cake with a small quantity of diethyl ether) and the filtrate concentrated in vacuo. The residue was partitioned between diethyl ether (100 ml) and 1 M sodium hydroxide (100 ml) and the organics discarded. The aqueous was washed with more diethyl ether and then cooled in an ice-water bath. The pH was adjusted to approximately 6 with 36% hydrochloric acid, and allowed to stand for 1 h. The resulting solid was collected by filtration and dried under vacuum to afford 2.2 g (85%) of the title compound as a grey solid: MS (ES$^+$) m/z 236 [M+H]$^+$.

g) 7-[2,4-Difluoro-3-(pyridin-3-yl)phenyl]-3-trifluoromethylimidazo[1,2-b][1,2,4]triazine A mixture of 7-bromo-3-trifluoromethylimidazo[1,2-b][1,2,4]triazine (0.1 g, 0.37 mmol), 2,4-difluoro-3-(pyridin-3-yl)benzeneboronic acid (132 mg, 0.56 mmol) and 2 M Na$_2$CO$_3$ (0.56 ml) in 1,2-dimethoxyethane (2 ml) was degassed for 10 min with a stream of nitrogen. Tetrakis(triphenylphosphine)palladium(0) (0.022 g) was added and the mixture was stirred under nitrogen at 80° C. for 12 h. After allowing to cool to ambient temperature, the mixture was diluted with ethyl acetate then partitioned between water (100 ml) and ethyl acetate (100 ml). The organic extracts were dried (MgSO$_4$), filtered and evaporated in vacuo. The residue was purified by flash chromatography (silica gel, 2.5% MeOH/CH$_2$Cl$_2$), to give 78 mg (55%) of the title compound: $^1$H NMR (400 MHz, CDCl$_3$) δ 7.17–7.22 (1H, m), 7.37–7.41 (1H, m), 7.80 (1H, d, J 8.4), 8.10–8.16 (1H, m), 8.56 (1H, d, J 2.6), 8.62 (1H, dd, J 4.6, 1.5), 8.72 (1H, 8.74 (1H, s); MS (ES$^+$) m/z 378 [M+H]$^+$.

EXAMPLE 5

7-[4-Methyl-3-(pyridin-3-yl)phenyl]-3-trifluoromethylimidazo[1,2-b][1,2,4]triazine a) 5,5-Dimethyl-2-(4-methyl-3-nitrophenyl)-[1,3,2]dioxaborinane

4-Bromo-2-nitrotoluene (2.20 g, 9.88 mmol) was reacted with bis(neopentyl glycolato)diboron (2.25 g, 9.96 mmol) by a similar procedure to that described in Example 2, step d, to give 0.52 g of the title compound as an off-white solid: $^1$H NMR (400 MHz, CDCl$_3$) δ 1.03 (6H, s), 2.60 (3H, s), 3.78 (4H, s), 7.30 (1H, d, J 7.7), 7.87 (1H, dd, J 1.0, 7.6), 8.35 (1H, d, J 0.7).

b) 7-(4-Methyl-3-nitrophenyl)-3-trifluoromethylimidazo[2-b][1,2,4]triazine

7-Bromo-3-trifluoromethylimidazo[1,2-b][1,2,4]triazine (0.30 g, 1.12 mmol), prepared in Example 4, step c, was reacted with 5,5-dimethyl-2-(4-methyl-3-nitrophenyl)-[1,3,2]dioxaborinane (0.29 g, 1.16 mmol) by a similar procedure to that described in Example 1, step e. Purification by chromatography (silica gel, 40–60% EtOAc/isohexane) gave 0.20 g of the title compound as a yellow solid: $^1$H NMR (400 MHz, CDCl$_3$) δ 2.70 (3H, s), 7.55 (1H, d, J 7.8), 8.21 (1H, dd, J 1.9, 7.8), 8.68 (1H, s), 8.83 (1H, d, J 1.9), 8.87 (1H, s); MS (ES$^+$) m/z 324 [M+H]$^+$.

c) 2-Methyl-5-(3-trifluoromethylimidazo[1,2-b][1,2,4]triazin-7-yl)phenylamine 7-(4-Methyl-3-nitrophenyl)-3-trifluoromethylimidazo[1,2-b][1,2,4]triazine (0.27 g, 0.83 mmol) was dissolved in EtOH/1,4-dioxane (20 ml, 1:1) at ambient temperature under an atmosphere of nitrogen and tin(II) chloride (0.80 g, 4.13 mmol) added. This stirred mixture was warmed at 50° C. for 6 h. The solvents were removed in vacuo, ice-water/NaHCO$_3$ was added and extracted with dichloromethane. These extracts were washed with water and saturated brine then dried (MgSO$_4$), filtered and concentrated in vacuo. Purification by chromatography (silica gel, dichloromethane) gave 0.24 g of the title compound as a red solid: $^1$H NMR (400 MHz, CDCl$_3$) δ 2.26 (3H, s), 3.75–3.85 (2H, br), 7.22 (1H, d, J 7.8), 7.40 (1H, dd, J 1.7, 7.8), 7.43 (1H, d, J 1.7), 8.55 (1H, s), 8.76 (1H, s); MS (ES$^+$) m/z 294 [M+H]$^+$.

d) 7-(3-Bromo-4-methylphenyl)-3-trifluoromethylimidazo[1,2-b][1,2,4]triazine 2-Methyl-5-(3-trifluoromethylimidazo[1,2-b][1,2,4]triazin-7-yl)phenylamine (0.12 g, 0.41 mmol) was bromodeaminated as described in Example 2, step d. Purification by chromatography (silica gel, dichloromethane) gave 0.03 g of the title compound as a yellow solid: $^1$H NMR (400 MHz, CDCl$_3$) δ 2.50 (3H, s), 7.41 (1H, d, J 8.0), 7.93 (1H, dd, J 1.8, 8.0), 8.33 (1H, d, J 1.8), 8.59 (1H, s), 8.84 (1H, s); MS (ES$^+$) m/z 357/359 [M+H]$^+$.

e) 7-[4-Methyl-3-(pyridin-3-yl)phenyl]-3-trifluoromethylimidazo[1,2-b][1,2,4]triazine 7-(3-Bromo-4-methylphenyl)-3-trifluoromethylimidazo[1,2-b][1,2,4]triazine (28 mg, 78 µmol) was dissolved in tetrahydrofuran (3 ml) under nitrogen and degassed for 10 min before 3-(tributylstannyl)pyridine (37 mg, 100 µmol) and tetrakis(triphenylphosphine)palladium(0) (10 mg, 9 µmol) were added. The stirred mixture was heated at 80° C. for 48 h. Solvent was removed in vacuo and the residue purified by chromatography (silica gel, 50% EtOAc/isohexane) to give 12 mg of the title compound as a yellow solid: $^1$H NMR (400 MHz, CDCl$_3$) δ 2.37 (3H, s), 7.40–7.44 (1H, m), 7.50 (1H, d, J 8.2), 7.71–7.75 (1H, m), 7.98 (1H, d, J 1.9), 8.03 (1H, dd, J 1.9, 8.0), 8.62 (1H, s), 8.65–8.68 (2H, m), 8.79 (1H, s); MS (ES$^+$) m/z 356 [M+H]$^+$.

EXAMPLE 6

6,2'-Difluoro-4'-hydroxy-5'-[3-(1-hydroxy-1-methylethyl)imidazo[1,2-b][1,2,4]triazin-7-yl]biphenyl-2-carbonitrile a) 2-(4-Fluoro-2-methoxyphenyl)-4,4,5,5-tetramethyl-[1,3,2]dioxaborolane

Conversion of 1-bromo-4-fluoro-2-methoxybenzene (WO 96/19458) to 2-(4-fluoro-2-methoxyphenyl)-4,4,5,5-tetramethyl-[1,3,2]dioxaborolane was carried out as described in Example 2, step a, in 44% yield: $^1$H NMR (400 MHz, CDCl$_3$) δ 1.34 (12H, s), 6.55–6.67 (2H, m), 7.65 (1H, t, J 8).

b) 2-[7-(4-Fluoro-2-methoxyphenyl)imidazo[1,2-b][1,2,4]triazin-3-yl]-propan-2-ol 2-(4-Fluoro-2-methoxyphenyl)-4,4,5,5-tetramethyl-[1,3,2]dioxaborolane was coupled to 2-(7-bromoimidazo[1,2-b][1,2,4]triazin-3-yl)propan-2-ol (from Example 1, step d) under the conditions described in Example 1, step e. The residue was purified by flash column chromatography (silica gel, EtOAc) to give the title compound in 91% yield: $^1$H NMR (400 MHz, CDCl$_3$) δ 1.70 (6H, s), 3.57 (1H, s), 3.87 (3H, s), 6.78–6.83 (2H, m), 7.87 (1H, dd, J 1.6, 6.6), 8.23 (1H, s), 8.69 (1H, s); MS (ES$^+$) m/z 303 [M+H]$^+$.

c) 2-[7-(5-Bromo-4-fluoro-2-methoxyphenyl)imidazo[1,2-b][1,2,4]triazin-3-yl]propan-2-ol To a cold (−20° C.) solution of 2-[7-(4-fluoro-2-methoxyphenyl)imidazo[1,2-b][1,2,4]triazin-3-yl]propan-2-ol (0.4 g, 1.32 mmol) in acetonitrile (4 ml) under nitrogen was added tetrafluoroboric acid (54 wt % solution in Et$_2$O, 0.21 ml, 1.59 mmol) and then N-bromosuccinimide (0.28 g, 1.59 mmol) slowly such that the internal temperature remained less than −10° C. After addition the cooling bath was removed and the reaction mixture was allowed to warm to room temperature. Stirring at this temperature continued for 16 h. A 40% aqueous solution of NaHSO$_3$ (10 ml) was added and the reaction mixture extracted with EtOAc (3×50 ml). Organic extracts were washed with water (50 ml), saturated aqueous brine (50 ml), dried (Na$_2$SO$_4$) and concentrated under reduced pressure. The residue was purified by flash chromatography (silica gel, EtOAc) to give a quantitative yield of the title compound: $^1$H NMR (400 MHz, CDCl$_3$) δ 1.71 (6H, s), 3.47 (1H, s), 3.89 (3H, s), 6.86 (1H, d, J 10.3), 8.21 (1H, d, J 7.9), 8.29 (1H, s), 8.74 (1H, s); MS (ES$^+$) m/z 381, 383 [M+H]$^+$.

d) 2-{7-[4-Fluoro-2-methoxy-5-(4,4,5,5-tetramethyl-[1,3,2]dioxaborolan-2-yl)phenyl]imidazo[1,2-b][1,2,4]triazin-3-yl}propan-2-ol Conversion of 2-[7-(5-bromo-4-fluoro-2-methoxyphenyl)imidazo[1,2-b][1,2,4]triazin-3-yl]propan-2-ol to 2-{7-[4-fluoro-2-methoxy-5-(4,4,5,5-tetramethyl-[1,3,2]dioxaborolan-2-yl)phenyl]imidazo[1,2-b][1,2,4]triazin-3-yl}propan-2-ol was carried out as described in Example 2, step a. The residue was purified by flash column chromatography (silica gel, 70% EtOAc/isohexane) to give 33% yield: $^1$H NMR (360 MHz, CDCl$_3$) δ 1.36 (12H, s), 1.70 (6H, s), 3.53 (1H, s), 3.85 (3H, s), 6.75 (1H, d, J 10.3), 8.10 (1H, d, J 7.9), 8.14 (1H, s), 8.67 (1H, s); MS (ES$^+$) m/z 429 [M+H]$^+$.

e) 6,2'-Difluoro-5'-[3-(1-hydroxy-1-methylethyl)imidazo[1,2-b][1,2,4]triazin-7-yl]-4'-methoxybiphenyl-2-carbonitrile 2-{7-[4-Fluoro-2-methoxy-5-(4,4,5,5-tetramethyl-[1,3,2]dioxaborolan-2-yl)phenyl]imidazo[1,2-b][1,2,4]triazin-3-yl}propan-2-ol was coupled to 2-bromo-3-fluorobenzonitrile (from Example 2, step a) under the conditions described in Example 1, step e. The residue was purified by flash column chromatography (silica gel, 3% isopropyl alcohol in dichloromethane) to give the title compound in 40% yield: $^1$H NMR (400 MHz, CDCl$_3$) δ 1.69 (6H, s), 3.53 (1H, s), 3.96 (3H, s), 6.96 (1H, d, J 10.3), 7.43–7.62 (3H, m), 8.11 (1H, d, J 7.9), 8.34 (1H, s), 8.71(1H, s); MS (ES$^+$) m/z 422 [M+H]$^+$ f) 6,2'-Difluoro-4'-hydroxy-5'-[3-(1-hydroxy-1-methylethyl)imidazo[1,2-b][1,2,4]triazin-7-yl]biphenyl-2-carbonitrile A solution of 6,2'-difluoro-5'-[3-(1-hydroxy-1-methylethyl)imidazo[1,2-b][1,2,4]triazin-7-yl]-4'-methoxybiphenyl-2-carbonitrile (0.18 g, 0.43 mmol) dissolved in anhydrous dichloromethane (10 ml) was cooled to −60° C. under nitrogen. Boron tribromide (2 M solution in dichloromethane, 1.28 ml, 2.57 mmol) was added with stirring. After 0.5 h the cooling bath was removed and the mixture was allowed to stir at room temperature for 4 h. Methanol (2 ml) was added and the mixture was shaken with 2 N NaOH (10 ml). Following neutralisation of the aqueous layer with 3 N HCl the solution was extracted with EtOAc (3×50 ml), dried (Na$_2$SO$_4$), filtered and evaporated to dryness. The residue was purified by flash column chromatography (silica gel, EtOAc) and crystallised from dichloromethane to give 28 mg (16%) of the title compound: $^1$H NMR (360 MHz, CDCl$_3$) δ 1.70 (6H, s), 3.38 (1H, br s), 3.96 (3H, s), 7.38–7.49 (3H, m), 7.59–7.61 (1H, dd, J 0.9, 7.4), 8.10 (1H, d, J 8.0) 8.52 (1H, s), 8.71 (1H, s), 8.90 (1H, s); MS (ES$^+$) m/z 408 [M+H]$^+$.

EXAMPLE 7

3'-[3-(1-Hydroxy-1-methylethyl)imidazo[1,2-b][1,2,4]triazin-7-yl]-4,2',6'-trifluorobiphenyl-2-carbonitrile A suspension of 2-bromo-5-fluorobenzonitrile (10.0 g, 50 mmol), potassium fluoride (9.59 g, 165 mmol) and 2,6-difluorophenylboronic acid (9.87 g, 62.5 mmol) in tetrahydrofuran (120 ml) and water (15 ml) was degassed with nitrogen for 30 min. Tris(dibenzylidineacetone)dipalladium (0) (916 mg, 1.0 mmol) and tri-tert-butylphosphine (10% w/w solution in hexane, 0.5 ml) were added and the mixture stirred at ambient temperature for 18 h. The black solution was washed with 1N sodium hydroxide solution (2×100 ml), and the aqueous phase was re-extracted with diethyl ether (100 ml). The organic layers were combined, washed with brine (50 ml), filtered through a glass microfibre filter paper then evaporated to give an orange solid. The solid was suspended in 2-propanol (120 ml) and heated to 70° C. to aid dissolution. The solution was left to cool to ambient temperature then water (120 ml) was added dropwise over 1 h. The resulting solid was collected by filtration, washed with 2-propanol/water (1:1, 30 ml) then dried under vacuum to give 4,2',6'-trifluorobiphenyl-2-carbonitrile (9.92 g, 85 %) as a grey solid: δ$_H$ (360 MHz, CDCl$_3$) 7.06 (2H, t, J 7.9), 7.38–7.52 (4H, m).

To a slurry of 4,2',6'-trifluorobiphenyl-2-carbonitrile (5.0 g, 21.4 mmol) and 1,3-dibromo-5,5-dimethylhydantoin (3.37 g, 11.8 mmol) in acetonitrile (45 ml) was added concentrated sulfuric acid (3.15 g, 32.2 mmol). The slurry was warmed to 70° C. and the resulting solution stirred for 7 h then aged at ambient temperature for 18 h. Water (45 ml) was added dropwise to the solution over 15 min. The layers were allowed to settle and the product rapidly crystallised. The slurry was left to stir for 0.5 h then the solid was collected by filtration, washed with 1:1 acetonitrile:water (10 ml) and left to air dry, which gave 3'-bromo-4,2',6'-trifluorobiphenyl- 2-carbonitrile (6.3 g, 94%) as a white solid: δ$_H$ (360 MHz, CDCl$_3$) 6.97–7.08 (1H, m), 7.38–7.54 (2H, m), 7.62–7.68 (1H, m).

3'-Bromo-4,2',6'-trifluorobiphenyl-2-carbonitrile (187 mg, 0.6 mmol), 2-(imidazo[1,2-b][1,2,4]triazin-3-yl)proplan-2-ol (hydrochloride salt) (107 mg, 0.5 mmol) and potassium acetate (123 mg, 1.25 mmol) were suspended in N,N-dimethylacetamide (2 ml) and degassed with nitrogen for 10 min. Palladium(II) acetate (5.6 mg, 0.025 mmol) and triphenylphosphine (6.6 mg, 0.025 mmol) were added and the mixture heated at 120° C. for 3 h. The mixture was allowed to cool to ambient temperature, then diluted with ethyl acetate (100 ml) and dichloromethane (100 ml). The organics were washed with water (50 ml) and brine (30 ml), dried over anhydrous sodium sulfate, filtered and evaporated to give an off-white solid. This solid was purified by flash column chromatography on silica, eluting with dichloromethane (+0.1% 0.880 ammonia) on a gradient of methanol (0–3%). Collecting appropriate fractions, followed by evaporation and trituration with diethyl ether (5 ml), gave 3'-[3-(1-hydroxy-1-methylethyl)imidazo[1,2-b][1,2,4]triazin-7-yl]-4,2',6'-trifluorobiphenyl-2-carbonitrile (156 mg, 76%) as a white solid: δ$_H$ (360 MHz, CDCl$_3$) 1.72 (6H, s), 3.21–3.24 (1H, m), 7.21–7.24 (1H, m), 7.43–7.48 (1H, m), 7.54–7.58 (2H, m), 8.27–8.30 (2H, m), 8.79 (1H, s); m/z (ES$^+$) 410 (M$^+$+H).

The invention claimed is:
1. A compound of the formula I, or a pharmaceutically acceptable salt thereof:

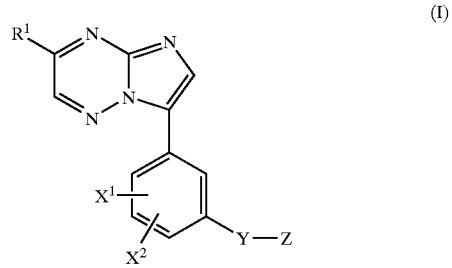

wherein:
X¹ represents $C_{1-6}$ alkyl, trifluoromethyl, hydroxy or $C_{1-6}$ alkoxy, and X² represents hydrogen; or
X¹ represents halogen, $C_{1-6}$ alkyl, trifluoromethyl, hydroxy or $C_{1-6}$ alkoxy, and X² represents halogen;
Y represents a chemical bond, an oxygen atom, or a —NH— linkage;
Z represents an optionally substituted aryl or heteroaryl group;
R¹ represents hydrogen, hydrocarbon, a heterocyclic group, halogen, cyano, trifluoromethyl, nitro, —OR$^a$, —SR$^a$, —SOR$^a$, SO$_2$R$^a$, —SO$_2$NR$^a$R$^b$, —NR$^a$R$^b$, —NR$^a$COR$^b$,—NR$^a$CO$_2$R$^b$, —COR$^a$, COR$_2$R$^a$, —CONR$^a$R$^b$ or CR$^a$=NOR$^b$; and
R$^a$ and R$^b$ independently represent hydrogen, hydrocarbon or a heterocyclic group.

2. The compound of claim 1 of the formula IIA, or a pharmaceutically acceptable salt thereof:

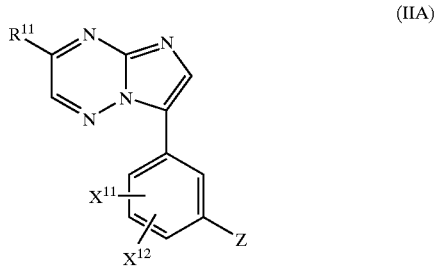

(IIA)

wherein:
X¹¹ represents methyl, trifluoromethyl, hydroxy or methoxy, and X¹² represents hydrogen; or
X¹¹ represents fluoro, chloro, methyl, trifluoromethyl, hydroxy or methoxy, and X¹² represents fluoro;
R¹¹ represents hydrogen, $C_{1-6}$ alkyl, halo($C_{1-6}$)alkyl, dihalo($C_{1-6}$)alkyl, hydroxy($C_{1-6}$)alkyl, dihydroxy($C_{1-6}$) alkyl, $C_{1-6}$alkoxy($C_{1-6}$)alkyl, di($C_{1-6}$)alkoxy($C_{1-6}$) alkyl, cyano($C_{1-6}$)alkyl, $C_{2-6}$alkoxycarbonyl($C_{1-6}$) alkyl, heteroaryl, $C_{1-6}$alkyl-heteroaryl, heteroaryl($C_{1-6}$) alkyl, halogen, cyano, trifluoromethyl, formyl, $C_{2-6}$alkylcarbonyl, $C_{2-6}$ alkoxycarbonyl or —CR⁴=NOR⁵;
R⁴ represents hydrogen or $C_{1-6}$ alkyl; and
R⁵ represents hydrogen, $C^{1-6}$ alkyl, hydroxy($C_{1-6}$)alkyl or di($C_{1-6}$)alkylamino($C_{1-6}$)alkyl.

3. The compound of claim 2 of the formula IIB, or a pharmaceutically acceptable salt thereof:

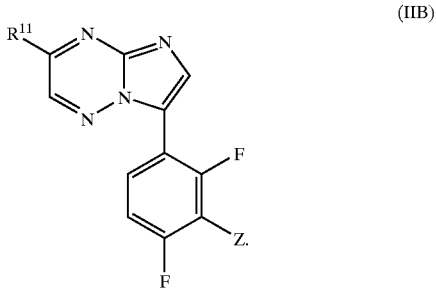

(IIB)

4. The compound of claim 2 of the formula IIC, or a pharmaceutically acceptable salt thereof:

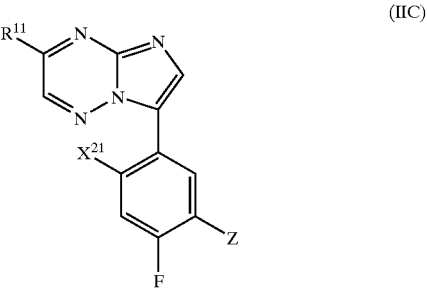

(IIC)

wherein:
X²¹ represents fluoro, chloro, methyl, trifluoromethyl, hydroxy or methoxy.

5. The compound of claim 2 of the formula IID, or a pharmaceutically acceptable salt thereof:

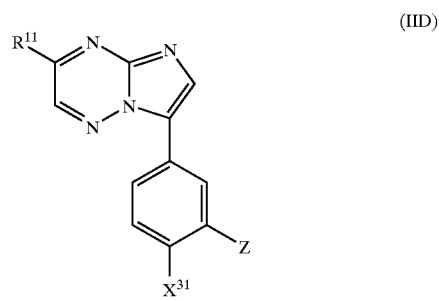

(IID)

wherein:
X³¹ represents methyl, trifluoromethyl, hydroxy or methoxy.

6. A compound which is selected from:
2-{7-[2,4-difluoro-3-(pyridin-4-yl)phenyl]imidazo[1,2-b][1,2,4]triazin-3-yl}propan-2ol;
3'-[3-(1-hydroxy-1-methylethyl)imidazo[1,2-b][1,2,4]triazin-7-yl]-6,2',6'-trifluorobiphenyl-2-carbonitrile;
3'-[3-(1-fluoro-1-methylethyl)imidazo[1,2-b][1,2,4]triazin-7-yl]-4,2',6'-trifluorobiphenyl-2-carbonitrile;
7-[2,4-difluoro-3-(pyridin-3-yl)phenyl]-3-trifluoromethylimidazo[1,2-b][1,2,4]triazine;
7-[4-methyl-3-(pyridin-3-yl)phenyl]-3-trifluoromethylimidazo[1,2-b][1,2,4]triazine;
6,2'-difluoro-4'-hydroxy-5'-[3-(1-hydroxy-1-methylethyl)imidazo[1,2-b[]1,2,4]triazin-7-yl]biphenyl-2-carbonitrile;
or a pharmaceutically acceptable salt thereof.

7. A compound which is selected from:
3'-[3-(1-hydroxy-1-methylethyl)imidazo[1,2-b][1,2,4]triazin-7-yl]-4,2',6'-trifluorobiphenyl-2-carbonitrile;
or a pharmaceutically acceptable salt thereof.

8. A pharmaceutical composition comprising a compound of claim 1 or a pharmaceutically acceptable salt thereof and a pharmaceutically acceptable carrier.

9. A method for the treatment of anxiety, which comprises administering to a patient in need of such treatment an effective amount of a compound of claim 1 or a pharmaceutically acceptable salt thereof.

10. A process for the preparation of the compound of claim 1, which comprises:

(A) reacting a compound of formula III with a compound of formula IV:

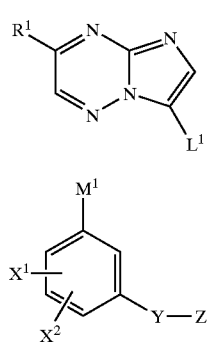

wherein $X^1$, $X^2$, Y, Z and $R^1$ are as defined in claim 1, $L^1$ represents a suitable leaving group, and $M^1$ represents a boronic acid moiety $—B(OH)_2$ or a cyclic ester thereof formed with an organic diol, or $M^1$ represents $—Sn(Alk)_3$ in which Alk represents $C_{1-6}$alkyl; in the presence of a transition metal catalyst; or (B) reacting a compound of formula V with a compound of formula VI:

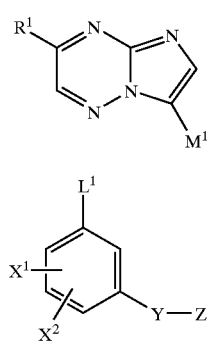

wherein $X^1$, $X^2$, Y, Z and $R^1$ are as defined in claim 1, and $L^1$ and $M^1$ are as defined above; in the presence of a transition metal catalyst; or (C) reacting a compound of formula VII with a compound of formula VIII:

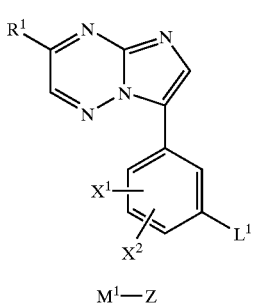

wherein $X^1$, $X^2$, Z and $R^1$ are as defined in claim 1, and $L^1$ and $M^1$ are as defined above; in the presence of a transition metal catalyst; or (D) reacting a compound of formula IX with a compound of formula X:

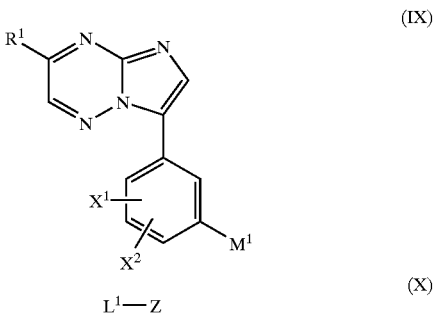

wherein $X^1$, $X^2$, Z and $R^1$ are as defined in claim 1, and $L^1$ and $M^1$ are as defined above; in the presence of a transition metal catalyst; or (E) reacting a compound of formula X as defined above with a compound of formula XI:

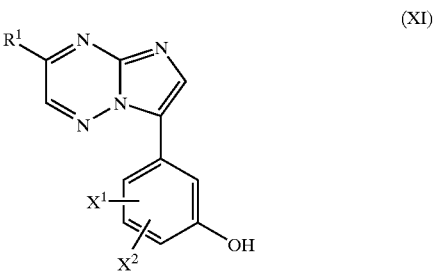

wherein $X^1$, $X^2$ and $R^1$ are as defined in claim 1; or (F) reacting a compound of formula X as defined above with a compound of formula XII:

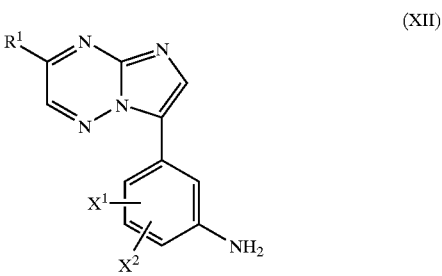

wherein $X^1$, $X^2$ and $R^1$ are as defined in claim 1; or (G) reacting a compound of formula XVI:

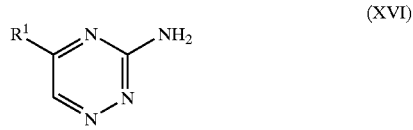

wherein $R^1$ is as defined in claim 1; with a compound of formula XVII:

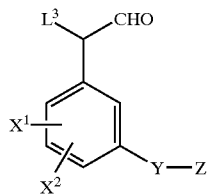

(XVII)

wherein $X^1$, $X^2$, Y and Z are as defined in claim 1, and $L^3$ represents a suitable leaving group; or (H) reacting a compound of formula XVIII with a compound of formula XIX:

$R^{1a}-M^1$ (XVIII)

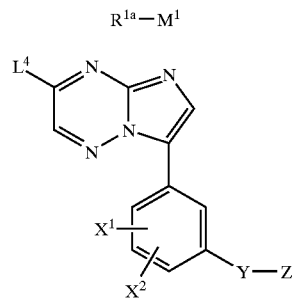

(XIX)

wherein $X^1$, $X^2$, Y and Z are as defined in claim 1, $M^1$ is as defined above, $R^{1a}$ represents an aryl or heteroaryl moiety, and $L^4$ represents a suitable leaving group; in the presence of a transition metal catalyst; or (J) reacting a compound of formula XII as defined above with 2,5-dimethoxytetrahydrofuran; or (K) reacting a compound of formula VI as defined above with a compound of formula XV:

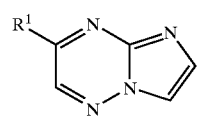

(XV)

wherein $R^1$ is as defined in claim 1; in the presence of a transition metal catalyst; and (L) subsequently, if required, converting a compound of formula I initially obtained into a further compound of formula I by standard methods.

* * * * *